United States Patent [19]
Kroll et al.

[11] Patent Number: 6,005,955
[45] Date of Patent: Dec. 21, 1999

[54] MIDDLE EAR TRANSDUCER

[75] Inventors: Kai Kroll, Minnetonka; Theodore P. Adams, Edina; Bruce A. Brillhart, Stillwater; Scott C. Meyerson, Mounds View, all of Minn.

[73] Assignee: St. Croix Medical, Inc., Minneapolis, Minn.

[21] Appl. No.: 08/693,436

[22] Filed: Aug. 7, 1996

[51] Int. Cl.$^6$ .................................................. H04R 25/00
[52] U.S. Cl. .............................. 381/328; 381/312; 600/25
[58] Field of Search .................................... 381/312, 322, 381/324, 328; 600/25

[56] References Cited

U.S. PATENT DOCUMENTS

| | | |
|---|---|---|
| 3,557,775 | 1/1971 | Mahoney . |
| 3,594,514 | 7/1971 | Wingrove . |
| 3,712,962 | 1/1973 | Epley . |
| 3,764,748 | 10/1973 | Branch et al. . |
| 3,931,648 | 1/1976 | Shea . |
| 3,940,974 | 3/1976 | Taylor . |
| 4,315,433 | 2/1982 | Edelman et al. . |
| 4,729,366 | 3/1988 | Schaefer et al. . |
| 4,774,933 | 10/1988 | Hough et al. . |
| 4,776,322 | 10/1988 | Hough et al. . |
| 4,817,607 | 4/1989 | Tatge . |
| 4,840,178 | 6/1989 | Heide et al. . |
| 4,850,962 | 7/1989 | Schaefer ................................. 600/25 |
| 4,957,478 | 9/1990 | Maniglia ................................. 600/25 |
| 5,012,520 | 4/1991 | Steeger . |
| 5,015,224 | 5/1991 | Maniglia ................................. 600/25 |
| 5,015,225 | 5/1991 | Hough et al. ........................... 600/25 |
| 5,163,957 | 11/1992 | Sade et al. . |
| 5,277,694 | 1/1994 | Leysieffer et al. ..................... 600/25 |
| 5,282,858 | 2/1994 | Bisch et al. ............................ 623/10 |
| 5,338,287 | 8/1994 | Miller et al. ........................... 600/25 |
| 5,360,388 | 11/1994 | Spindel et al. ......................... 600/25 |
| 5,411,467 | 5/1995 | Hortmann et al. ..................... 600/25 |
| 5,456,654 | 10/1995 | Ball ........................................ 600/25 |
| 5,498,226 | 3/1996 | Lenkauskas ........................... 600/25 |
| 5,531,787 | 7/1996 | Lesinski et al. . |
| 5,554,096 | 9/1996 | Ball ........................................ 600/25 |
| 5,624,376 | 4/1997 | Ball et al. .............................. 600/25 |

FOREIGN PATENT DOCUMENTS

| | | |
|---|---|---|
| 2365267 | 4/1978 | France . |
| WO 92/08330 | 5/1992 | WIPO . |
| WO 94/17645 | 8/1994 | WIPO . |

OTHER PUBLICATIONS

Suzuki, J.I., et al., "Early Studies and the History of Development of the Middle Ear Implant in Japan," Advances in Audiology (Karger, Basel), 4:1–14, (1988).

Suzuki, J.I., et al., "Principle, Construction and Indication of the Middle Ear Implant," Advances in Audiology, 4:15–21, (1988).

Goode, M.D., R.L., "Electromagnetic Implantable Hearing Aids," Advances in Audiology (Karger, Basel), 4:22–31, (1988).

Heide, J., et al., "Development of a Semi–Implantable Hearing Device," Advances in Audiology (Karger, Basel), 4:32–43, (1988).

(List continued on next page.)

*Primary Examiner*—Minsun Oh Harvey
*Attorney, Agent, or Firm*—Patterson & Keough, P.A.

[57] ABSTRACT

An electromechanical transducer for an implantable hearing aid, such as a partial middle ear implantable (P-MEI) or total middle ear implantable (T-MEI) hearing aid system. The invention comprises at least one piezoelectric element proportioned for mechanically coupling to a middle ear only through an auditory element in the middle ear, such as the tympanic membrane, malleus, incus, stapes, or in the inner ear, such as the oval window, round window, vestibule, or semicircular canals. The invention need not be secured to a temporal bone. Inertial masses and a carrier are optionally provided to assist in sensing or producing mechanical vibrations. The carrier is optionally hermetically sealed. Superpositioned individual frequency responses optimize an overall frequency bandwidth.

7 Claims, 22 Drawing Sheets

OTHER PUBLICATIONS

Tjellström, A., "Vibratory Stimulation of the Cochlea through a Percutaneous Transducer," Advances in Audiology (Karger Basel), 4:44–50, (1988).

Ohno, T., et al., "Structure and Performance of the Main Components," Advances in Audiology (Karger, Basel), 4:52–72, (1988).

Ikeda, H., et al., "Energy Source for the Middle Ear Implant," Advances in Audiology (Karger, Basel), 4:73–84, (1988).

Ohno, T., et al., "Performance of the Middle Ear Implants," Advances in Audiology (Karger, Basel), 4:85–96, (1988).

Kodera, K., et al., "Evaluation of the Ceramic Vibrator in the Cat," Advances in Audiology (Karger, Basel), 4:97–106, (1988).

Gyo, K., et al., "Measurement of Stapes Vibration Driven by the Ceramic Vibrator of a Middle Ear Implant–Human Temporal Bone Experiments," Advances in Audiology (Karger, Basel), 4:107–116, (1988).

Kodera, M.D., K., et al., "Evaluation of the Implantable Microphone in the Cat," Advances in Audiology (Karger, Basel), 4:117–123, (1988).

Yanagihara, N., et al., "Intraoperative Assessment of Vibrator–Induced Hearing," Advances in Audiology, 4:124–133, (1988).

Hiki, S., et al., "Audiological Evaluation of the Middle Ear Implant," Advances in Audiology (Karger, Basel), 4:134–148, (1988).

Yanagihara, N., et al., "Efficacy of the Partially Implantable Middle Ear Implant in Middle and Inner Ear Disorders," Advances in Audiology, 4:149–159, (1988).

Suzuki, J.I., et al., "Implantation of Partially Implantable Middle Ear Implant and the Indication," Advances in Audiology (Karger, Basel), 4:160–166 (1988).

Middle Ear Implant: Implantable Aids, Advance in Audiology, ol. 4, M. Hoke Editor, arger, 1–169, 1988.

T. Dumon, et al., "Piezoelectric Middle Ear Implant: Experimental Results", Abstract of Paper Presented at International Symposium on Electronic Implants in Otology and Conventional Hearing Aids, Walt Disney World Swan, Abstract #35, Nov. 11–14, 1996.

. . rederickson, et al., "Ongoing Investigations into an Implantable Electromagnetic Hearing Aid for Moderate to Sever into Sensorineural Hearing Loss", Otolaryngological Clinics of North America, vol. 28, No. 1, 107–121, Feb. 1995.

K.. Gyo, et al., "Sound Pickup Utilizing an Implantable Piezpelectric Ceramic Bimorph Element: Application to the Cochlear Implant", American Journal of Otology, vol. 5, No. 4, 273–276, Apr. 1987.

K. Gyo, et al., "Stapes Vibration Produced by the Output Transducer of an Implantable Hearing Aid", Arch Otolaryngol Head Neck Surg., vol. 113, 1078–1081, Oct. 1987.

G. Jako, "Biomedical Engineering in Ear Surgery", Otolaryngological Clinics of North America, vol. 5, No. 1, 173–182, Feb. 1972.

Wen H. Ko, et al., "Engineering Principles of Mechanical Stimulation of the Middle Ear", Otolaryngological Clinics of North America, vol. 28, No. 1, 29–41, Feb. 1995.

K. Kodera, et al., "Sound Evaluation of Partially Implantable Piezoelectric Middle Ear Implant: Comparative Study of frequency Responses", ENT Journal, vol. 73, No. 2, 108–111, Feb. 1994.

A. J. Maniglia, et al., "A Contactless Electromagnetic Implantable Middle Ear Sevice for Sensorineural Hearing Loss", ENT Journal, vol. 73, No. 2, 78–90, Feb. 1994.

A. J. Maniglia, et al., "Contactless, Semi–Implantable Electromagnetic Hearing Device for the treatment of Sensorineural Hearing Loss", Abstract of Paper Presented at International Symposium on Electronic Implants in Otology and Conventional Hearing Aids, Nov. 11–14, 1993.

Jun–Ichi Suzuki, et al., "Long–Term Clinical Resilts of the Partially Implantable Piezoelectric Middle Ear Implant", ENT Journal, vol. 73, No. 2, 104–107, Feb. 1994.

M. Tos, et al., "Implantation of Electromagnetic Ossicular Replacement Device", ENT Journal, vol. 73, No. 2, 93–103, Feb. 1993.

D.B. Welling, et al., "Auditory Stimulation og the Inner Ear via Semicircular Canals", Abstract of paper presented at International Symposium on Electronic Implants in otology and Conventional Hearing Aids, Walt Disney World Swan Abstract #9, Nov. 11–14, 1993.

N. Yanagihara, et al., "Partially Implantable Hearing Aid using Piezoelectric Ceramic Ossicular Vibrator", Abstract of Paper Presented at International Symposium on Electronic Implants in Otology and Conventional Hearing Aids, Walt Disnry World Swan #26, Nov. 11–14, 1993.

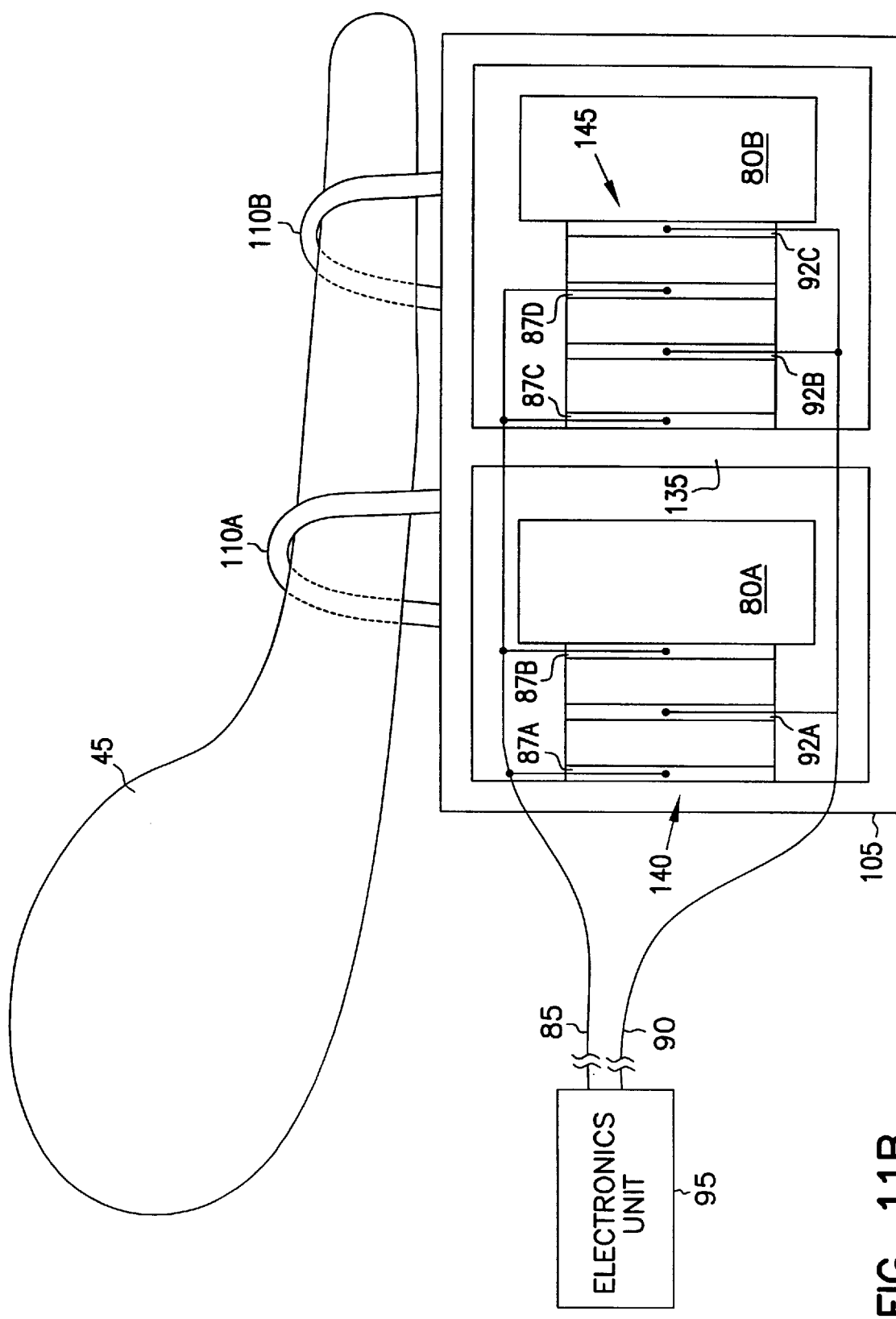

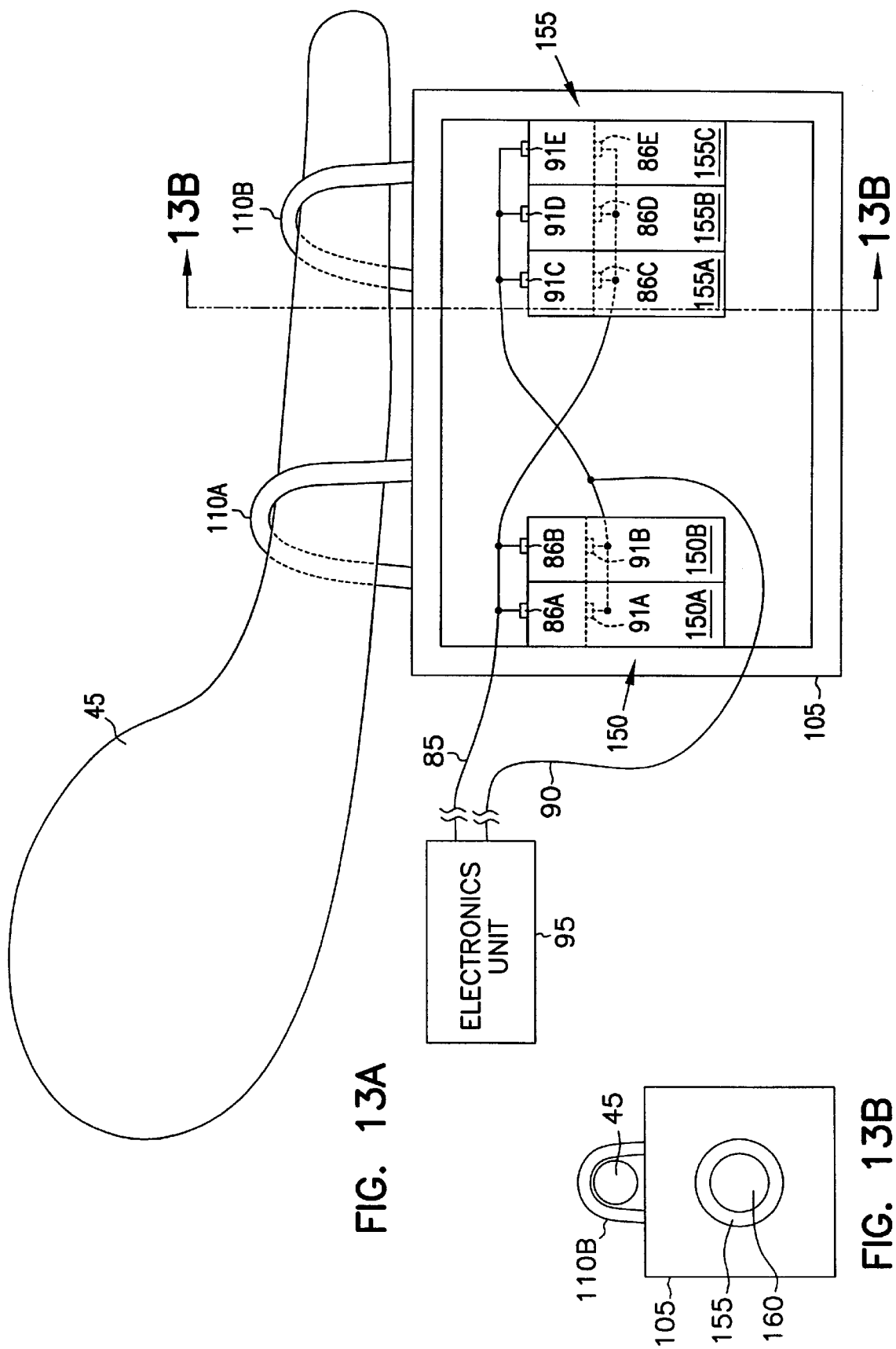

MIDDLE EAR TRANSDUCER

THE FIELD OF THE INVENTION

This invention relates to an electromechanical transducer for use in a hearing system at least partially implantable in a middle ear.

BACKGROUND

In some types of partial middle ear implantable (P-MEI) or total middle ear implantable (T-MEI) hearing aid systems, sounds produce mechanical vibrations which are transduced by an electromechanical input transducer into electrical signals. These electrical signals are in turn amplified and applied to an electromechanical output transducer. The electromechanical output transducer vibrates an ossicular bone in response to the applied amplified electrical signals to improve hearing.

Such electromechanical input and output transducers should be proportioned to provide convenient implantation in the middle ear. Low power consumption transducers are also desired for use with a limited longevity implanted battery as a power source, such as for T-MEI hearing aid systems.

SUMMARY OF THE INVENTION

The invention provides an electromechanical transducer for an implantable hearing aid, such as a partial middle ear implantable (P-MEI) or total middle ear implantable (T-MEI) hearing aid system. The transducer comprises a piezoelectric element proportioned for mechanical coupling to a middle ear only through an auditory element in the middle ear. More particularly, the invention provides convenient piezoelectric input and output electromechanical transducers, each mounted only to the auditory element for which vibrations are transduced. The invention does not require mounting a transducer to the temporal bone. This minimizes the invasive complexity of the surgical implantation procedure, and also minimizes steady state forces applied to the auditory element.

For sensing mechanical vibrations, an electromechanical input transducer is coupled only to a vibrating auditory element, such as a tympanic membrane, malleus, or incus. The vibrating auditory element is optionally mechanically isolated from an auditory element vibrated by an electromechanical output transducer. For vibrating an auditory element, an electromechanical output transducer is coupled only to a vibrated auditory element, such as an incus, stapes, oval window, round window, vestibule, or semicircular canal.

Piezoelectric elements used in the electromechanical input and output transducers comprise ceramic piezoelectric single element transducers, ceramic piezoelectric bi-element transducers, piezoelectric stacked transducers comprising multiple mechanically stacked subelements, piezoelectric film transducers, and piezoelectric film bi-element transducers.

Certain embodiments include an inertial mass used in conjunction with the piezoelectric elements for transducing between electrical signals and mechanical vibrations.

An overall electrical-to-mechanical or mechanical-to-electrical frequency response is optimized by superpositioning substantially nonidentical frequency responses of piezoelectric elements in combination with any accompanying inertial masses. Different frequency responses are obtained by using different masses, different piezoelectric elements, or other techniques.

In certain embodiments, a carrier is provided to support the piezoelectric elements and any accompanying inertial masses. The carrier is secured only to the auditory element for which vibrations are transduced. The carrier is optionally hermetically sealed to protect the piezoelectric elements and inertial masses.

Thus, the invention provides convenient piezoelectric input and output electromechanical transducers, each mounted only to the auditory element for which vibrations are transduced.

BRIEF DESCRIPTION OF THE DRAWINGS

In the drawings, like numerals describe like components throughout the several views.

FIG. 11B is a cross-sectional illustration of an alternative embodiment, to FIG. 11A, having electrical connections across a length of each transducer subelement.

FIG. 13A is a cross-sectional illustration of an eleventh embodiment of the invention, including a carrier and also including two stacked transducers having cylindrically hollowed cores.

FIG. 13B is a cross-sectional view taken along the cut line illustrated in FIG. 13A.

DESCRIPTION OF THE PREFERRED EMBODIMENTS

Figure 1:
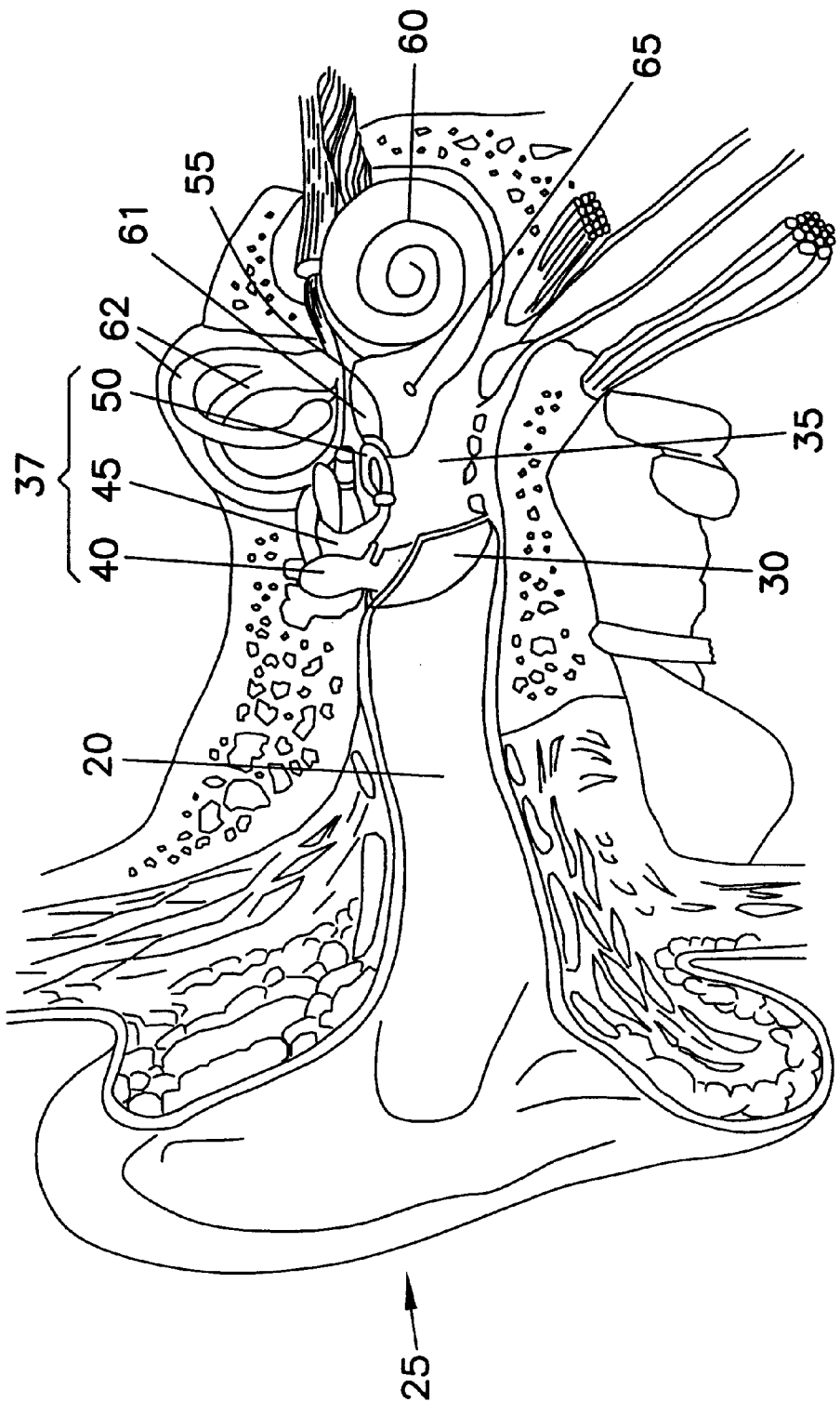
FIG. 1 illustrates a frontal section of an anatomically normal human right ear.

The invention provides an electromechanical transducer which is particularly advantageous when used in a middle ear implantable hearing aid system such as a partial middle ear implantable (P-MEI), total middle ear implantable (T-MEI), or other hearing aid system. A P-MEI or T-MEI hearing aid system assists the human auditory system in converting acoustic energy contained within sound waves into electrochemical signals delivered to the brain and interpreted as sound. FIG. 1 illustrates generally the use of the invention in a human auditory system. Sound waves are directed into an external auditory canal 20 by an outer ear (pinna) 25. The frequency characteristics of the sound waves are slightly modified by the resonant characteristics of the external auditory canal 20. These sound waves impinge upon the tympanic membrane (eardrum) 30, interposed at the terminus of the external auditory canal, between it and the tympanic cavity (middle ear) 35. Variations in the sound waves produce tympanic vibrations. The mechanical energy of the tympanic vibrations is communicated to the inner ear, comprising cochlea 60, vestibule 61, and semicircular canals 62, by a sequence of articulating bones located in the middle ear 35. This sequence of articulating bones is referred to generally as the ossicular chain 37. Thus, the ossicular chain transforms acoustic energy at the eardrum to mechanical energy at the cochlea 60.

The ossicular chain 37 includes three primary components: a malleus 40, an incus 45, and a stapes 50. The malleus 40 includes manubrium and head portions. The manubrium of the malleus 40 attaches to the tympanic membrane 30. The head of the malleus 40 articulates with one end of the incus 45. The incus 45 normally couples mechanical energy from the vibrating malleus 40 to the stapes 50. The stapes 50 includes a capitulum portion, comprising a head and a neck, connected to a footplate portion by means of a support crus comprising two crura. The stapes 50 is disposed in and against a membrane-covered opening on the cochlea 60. This membrane-covered opening between the cochlea 60 and middle ear 35 is referred to as the oval window 55. Oval window 55 is considered part of cochlea 60 in this patent application. The incus 45 articulates the capitulum of the stapes 50 to complete the mechanical transmission path.

Normally, prior to implantation of the invention, tympanic vibrations are mechanically conducted through the malleus 40, incus 45, and stapes 50, to the oval window 55. Vibrations at the oval window 55 are conducted into the fluid-filled cochlea 60. These mechanical vibrations generate fluidic motion, thereby transmitting hydraulic energy within the cochlea 60. Pressures generated in the cochlea 60 by fluidic motion are accommodated by a second membrane-covered opening on the cochlea 60. This second membrane-covered opening between the cochlea 60 and middle ear 35 is referred to as the round window 65. Round window 65 is considered part of cochlea 60 in this patent application. Receptor cells in the cochlea 60 translate the fluidic motion into neural impulses which are transmitted to the brain and perceived as sound. However, various disorders of the tympanic membrane 30, ossicular chain 37, and/or cochlea 60 can disrupt or impair normal hearing.

Hearing loss due to damage in the cochlea is referred to as sensorineural hearing loss. Hearing loss due to an inability to conduct mechanical vibrations through the middle ear is referred to as conductive hearing loss. Some patients have an ossicular chain 37 lacking sufficient resiliency to transmit mechanical vibrations between the tympanic membrane 30 and the oval window 55. As a result, fluidic motion in the cochlea 60 is attenuated. Thus, receptor cells in the cochlea 60 do not receive adequate mechanical stimulation. Damaged elements of ossicular chain 37 may also interrupt transmission of mechanical vibrations between the tympanic membrane 30 and the oval window 55.

Various techniques have been developed to remedy hearing loss resulting from conductive or sensorineural hearing disorder. For example, tympanoplasty is used to surgically reconstruct the tympanic membrane 30 and establish ossicular continuity from the tympanic membrane 30 to the oval window 55. Various passive mechanical prostheses and implantation techniques have been developed in connection with reconstructive surgery of the middle ear 35 for patients with damaged elements of ossicular chain 37. Two basic forms of prosthesis are available: total ossicular replacement prostheses (TORP), which is connected between the tympanic membrane 30 and the oval window 55; and partial ossicular replacement prostheses (PORP), which is positioned between the tympanic membrane 30 and the stapes 50.

Various types of hearing aids have been developed to compensate for hearing disorders. A conventional "air conduction" hearing aid is sometimes used to overcome hearing loss due to sensorineural cochlear damage or mild conductive impediments to the ossicular chain 37. Conventional hearing aids utilize a microphone, which transduces sound into an electrical signal. Amplification circuitry amplifies the electrical signal. A speaker transduces the amplified electrical signal into acoustic energy transmitted to the tympanic membrane 30. However, some of the transmitted acoustic energy is typically detected by the microphone, resulting in a feedback signal which degrades sound quality. Conventional hearing aids also often suffer from a significant amount of signal distortion.

Implantable hearing aid systems have also been developed, utilizing various approaches to compensate for hearing disorders. For example, cochlear implant techniques implement an inner ear hearing aid system. Cochlear implants electrically stimulate auditory nerve fibers within the cochlea 60. A typical cochlear implant system includes an external microphone, an external signal processor, and an external transmitter, as well as an implanted receiver and an implanted single channel or multichannel probe. A single channel probe has one electrode. A multichannel probe has an array of several electrodes. In the more advanced multichannel cochlear implant, a signal processor converts speech signals transduced by the microphone into a series of sequential electrical pulses corresponding to different frequency bands within a speech frequency spectrum. Electrical pulses corresponding to low frequency sounds are delivered to electrodes that are more apical in the cochlea 60. Electrical pulses corresponding to high frequency sounds are delivered to electrodes that are more basal in the cochlea 60. The nerve fibers stimulated by the electrodes of the cochlear implant probe transmit neural impulses to the brain, where these neural impulses are interpreted as sound.

Other inner ear hearing aid systems have been developed to aid patients without an intact tympanic membrane 30, upon which "air conduction" hearing aids depend. For example, temporal bone conduction hearing aid systems produce mechanical vibrations that are coupled to the cochlea 60 via a temporal bone in the skull. In such temporal bone conduction hearing aid systems, a vibrating element can be implemented percutaneously or subcutaneously.

A particularly interesting class of hearing aid systems includes those which are configured for disposition principally within the middle ear 35 space. In middle ear implantable (MEI) hearing aids, an electrical-to-mechanical output transducer couples mechanical vibrations to the ossicular chain 37, which is optionally interrupted to allow coupling of the mechanical vibrations to the ossicular chain 37. Both electromagnetic and piezoelectric output transducers have been used to effect the mechanical vibrations upon the ossicular chain 37.

One example of a partial middle ear implantable (P-MEI) hearing aid system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to the incus 45. Such electromagnetic output transducers have relatively high power consumption, which limits their usefulness in total middle ear implantable (T-MEI) hearing aid systems.

A piezoelectric output transducer is also capable of effecting mechanical vibrations to the ossicular chain 37. An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus 40, transducing mechanical energy into an electrical signal, which is amplified and further processed. A resulting electrical signal is provided to an electrical-to-mechanical piezoelectric output transducer that generates a mechanical vibration coupled to an element of the ossicular chain 37 or to the oval window 55 or round window 65. In the '366 patent, the ossicular chain 37 is interrupted by removal of the incus 45. Removal of the incus 45 prevents the mechanical vibrations delivered by the piezoelectric output transducer from mechanically feeding back to the piezoelectric input transducer.

Piezoelectric output transducers have several advantages over electromagnetic output transducers. The smaller size or volume of the piezoelectric output transducer advantageously eases implantation into the middle ear 35. The lower power consumption of the piezoelectric output transducer is particularly attractive for T-MEI hearing aid systems, which include a limited longevity implanted battery as a power source.

A piezoelectric output transducer is typically implemented as a ceramic piezo electric bi-element transducer, which is a cantilevered double plate ceramic element in which two opposing plates are bonded together such that they amplify a piezo electric action in a direction normal to the bonding plane. Such a bi-element transducer vibrates according to a potential difference applied between two bonded plates. A proximal end of such a bi-element transducer is typically cantilevered from a transducer mount which is secured to a temporal bone within the middle ear. A distal end of such a bi-element transducer couples mechanical vibrations to an ossicular element such as stapes 50. However, securing a bi-element transducer mount to the temporal bone adds invasive complexity to the surgical implantation procedure.

Figure 2:
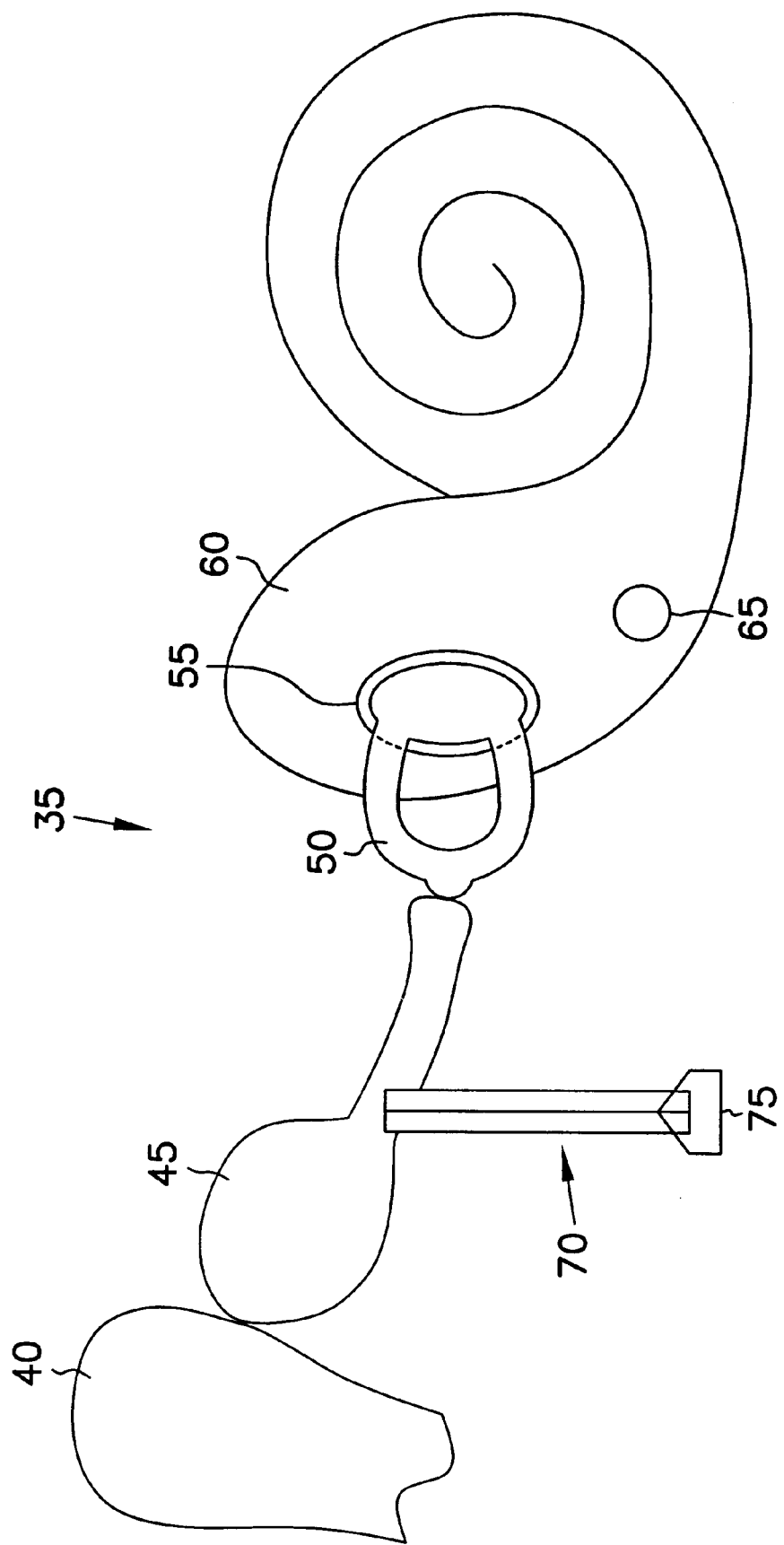
FIG. 2 is a cross-sectional illustration of a typical use of a bi-element transducer coupled to an auditory element in the middle ear.

FIG. 2 is a generalized illustration of a bi-element transducer 70 cantilevered at its proximal end from a mount 75 secured to a temporal bone within middle ear 35. A distal end of bi-element transducer 70 is mechanically coupled to an auditory element to receive or effect mechanical vibrations when operating as an input or output transducer respectively. For example, to receive mechanical vibrations as an input transducer, bi-element transducer 70 may be coupled to an auditory element such as tympanic membrane 30, malleus 40, or incus 45. In another example, to effect vibrations as an output transducer, bi-element transducer 70 may be coupled to an auditory element such as incus 45, stapes 50, oval window 55, round window 65, vestibule 61, or semicircular canal 62. However, mounting bi-element transducer 70 to the temporal bone adds invasive complexity in its surgical implantation.

The invention provides convenient piezoelectric input and output electromechanical transducers, each mounted only to the auditory element for which vibrations are transduced. In particular, the invention does not require mounting a transducer to the temporal bone. This minimizes the invasive complexity of the surgical implantation procedure, and also minimizes steady state forces applied to the auditory element.

Figure 3:
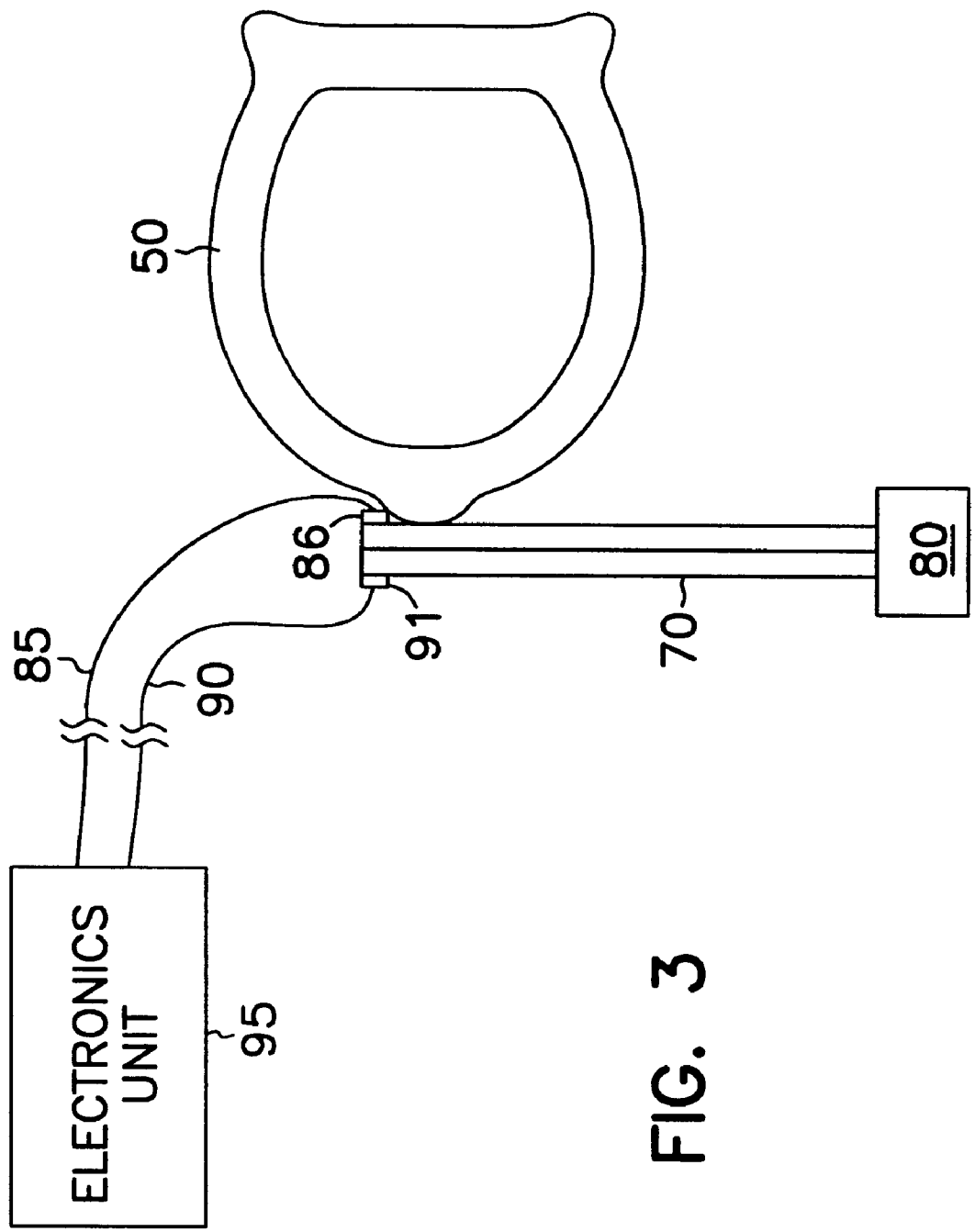
FIG. 3 is a cross-sectional illustration of a first embodiment of the invention, including a bi-element transducer secured only to a vibrated auditory element.

FIG. 3 illustrates generally a cross-sectional view of a first embodiment of the invention used as an electromechanical output transducer. A piezoelectric element, more particularly bi-element transducer 70, is mechanically coupled, and preferably secured, at its proximal end to middle ear 35 only through an auditory element, preferably stapes 50, or alternatively incus 45, stapes 50, oval window 55, round window 65, vestibule 61, or semicircular canals 62. Bi-element transducer 70 is secured only to stapes 50 by any known attachment technique, including biocompatible adhesives or mechanical fasteners. For example, in one embodiment, a deformable wire secured to the proximal end of bi-element transducer 70 is looped through an inner portion of stapes 50 and crimped to secure bi-element transducer 70 to stapes 50. The exact technique of attachment to the auditory element is not part of the invention, except that the piezoelectric element should be coupled only to the vibrated auditory element; it need not be secured elsewhere within the middle ear 35 such as to the temporal bone.

An inertial mass 80 is secured to a distal end of bi-element transducer 70 by any known attachment technique, including a biocompatible adhesive or mechanical fastener. Inertial mass 80 is of a biocompatible material such as titanium or stainless steel, or any other biocompatible material proportioned to provide sufficient inertial mass to impart a force upon stapes 50, as explained below.

Electronics unit 95 couples an electrical signal through lead wires 85 and 90 to any convenient respective connection points 86 and 91 on respective opposing elements of bi-element transducer 70. Electronics unit 95 and lead wires 85 and 90 are not part of the invention, but rather show how the invention is used in conjunction with a P-MEI, T-MEI, or other hearing aid system.

In response to the electrical signals received from electronics unit 95, bi-element transducer 70 bends with respect to a longitudinal plane between its opposing elements. The bending is resisted by inertial mass 80, thus mechanically coupling a force to stapes 50 through bi-element transducer 70. This force upon stapes 50 is in turn transmitted to cochlea 60 at oval window 55.

Figure 4:
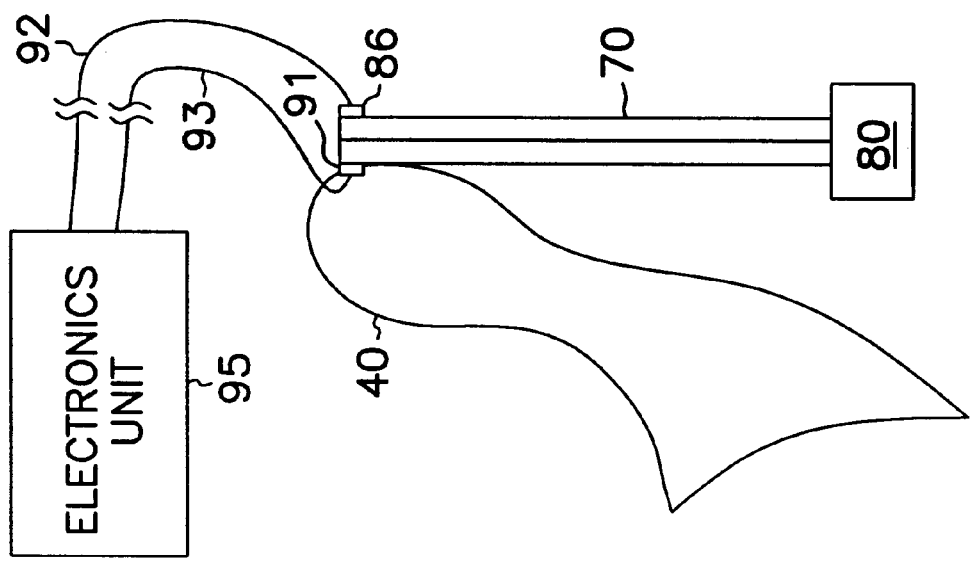
FIG. 4 is a cross-sectional illustration of a second embodiment of the invention, including a bi-element transducer secured only to a vibrating auditory element.

FIG. 4 illustrates generally a cross-sectional view of a second embodiment of the invention used as an electromechanical input transducer. A piezoelectric element, such as bi-element transducer 70, is secured by any known attachment technique at its proximal end, such as described above, only to malleus 40. Bi-element transducer 70 may also be secured only to other auditory elements for receiving mechanical vibrations, such as incus 45 or tympanic membrane 30. Vibrations of malleus 40 cause, at the proximal end of bi-element transducer 70, vibratory displacements that are opposed by inertial mass 80. As a result, bi-element transducer 70 bends with respect to the longitudinal plane between its opposing elements. A resulting electrical signal is provided at any convenient connection points 86 and 91 on respective opposing elements of bi-element transducer 70, through respective lead wires 92 and 93 to electronics unit 95.

Figure 5:
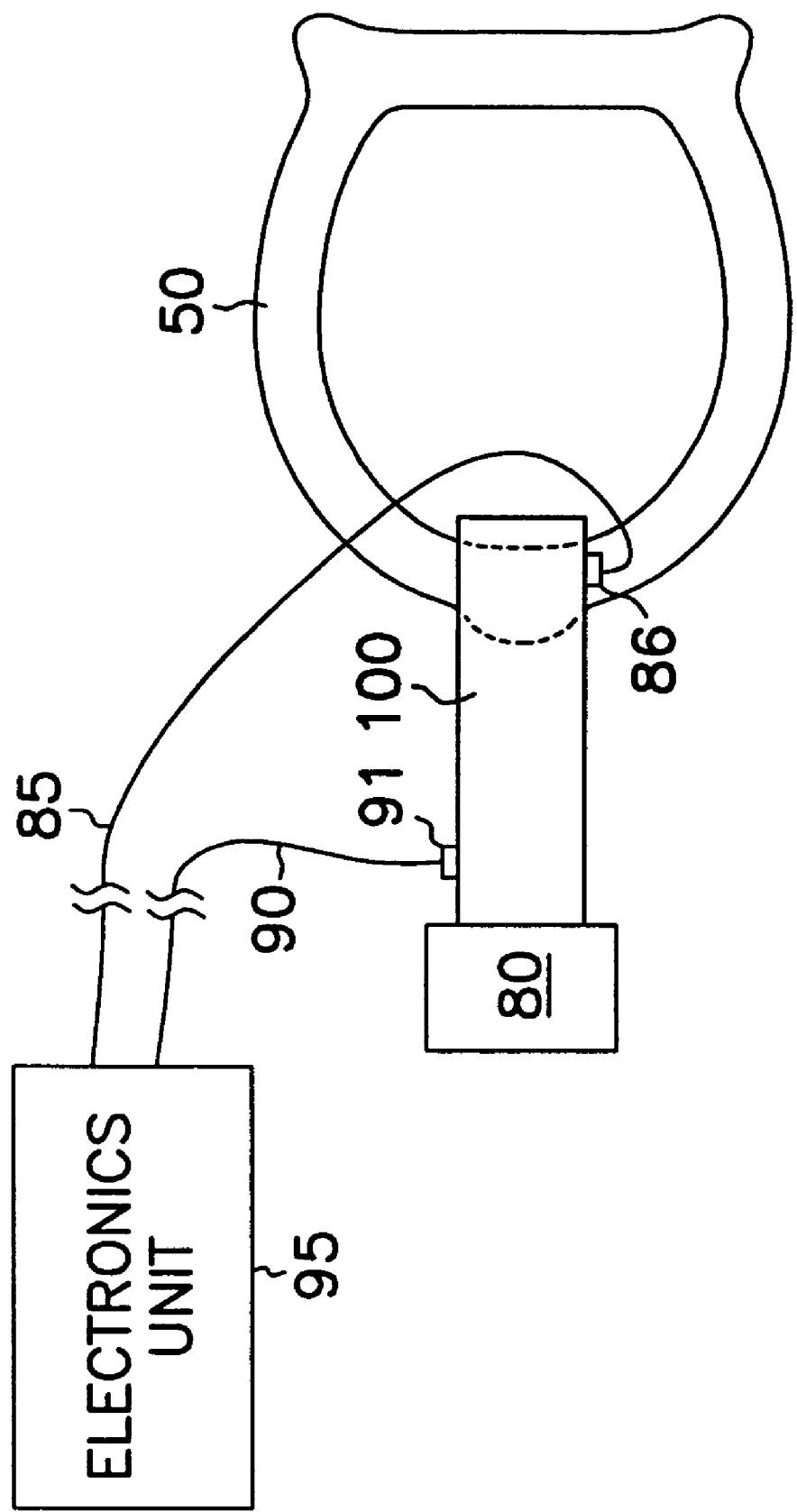
FIG. 5 is a cross-sectional illustration of a third embodiment of the invention, using a single element transducer secured only to a vibrated auditory element.

FIG. 5 illustrates generally a cross-sectional view of a third embodiment of the invention, used as an electromechanical output transducer, as described above. A piezoelectric element, such as ceramic single element transducer 100 is secured at its proximal end only to an auditory element, such as stapes 50. Any known attachment technique may be used, such as described above. An inertial mass 80, described above, is secured to a distal end of single element transducer 100 by any known attachment technique, such as described above.

This embodiment uses a piezoelectric effect with displacement approximately orthogonal to the direction of an applied electrical input signal, although a piezoelectric effect in another direction may also be used at the designer's discretion by rearranging the connection points accordingly. Electronics unit 95 delivers an electrical signal through lead wires 85 and 90 to any convenient respective connection points 86 and 91 on respective opposing faces of single element transducer 100. In response to this electrical signal, single element transducer 100 expands and contracts in a longitudinal direction between its proximal and distal ends. This vibratory displacement is resisted by inertial mass 80, thus coupling a force to stapes 50 through single element transducer 100. In a further embodiment, transducer 100 of FIG. 5 comprises a stack of multiple piezoelectric subelements connected mechanically in series, and wired electrically in parallel for increased vibratory displacement. In another further embodiment, inertial mass 80 is omitted; the distributed mass of transducer 100 mechanically couples a vibratory force to stapes 50.

Figure 6:
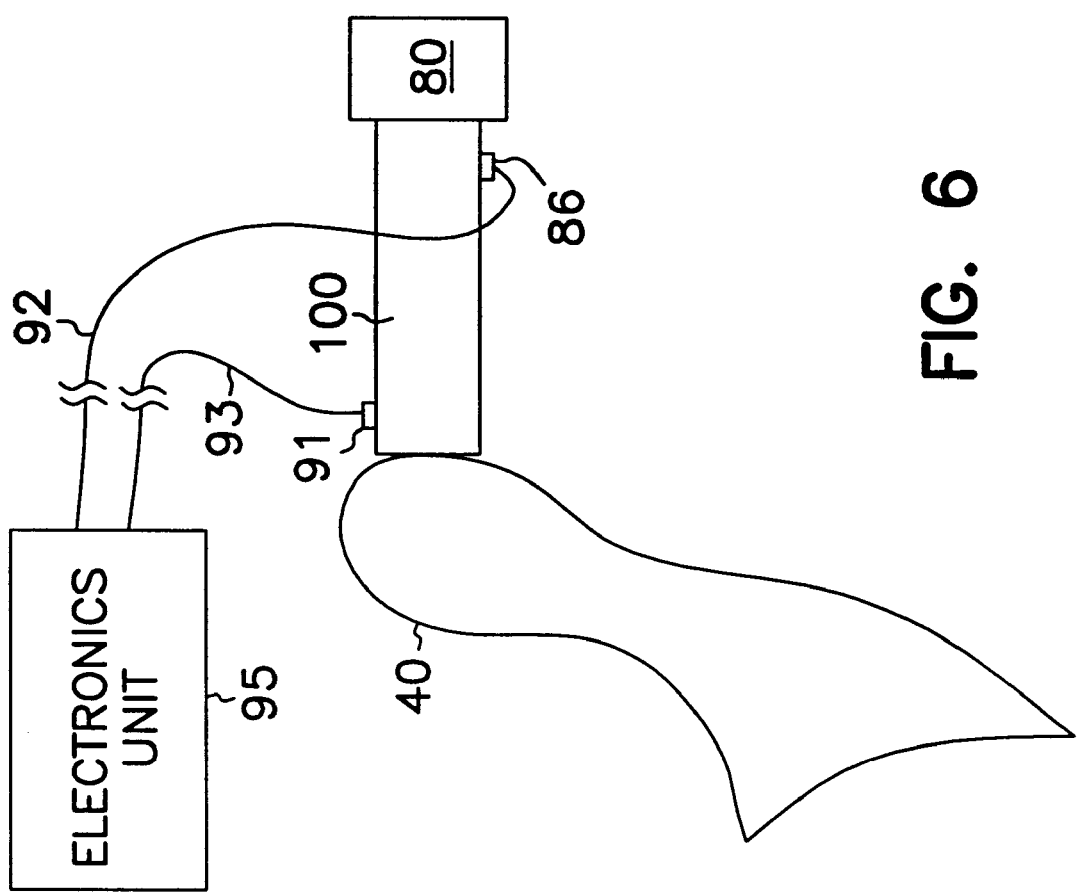
FIG. 6 is a cross-sectional illustration of a fourth embodiment of the invention, using a single element transducer secured only to a vibrating auditory element.

FIG. 6 illustrates generally a cross-sectional view of a fourth embodiment of the invention, used as an electromechanical input transducer, as described above. Single element transducer 100 is secured at its proximal end by any known attachment technique, such as described above, only to malleus 40 or other vibrating auditory element as described above. Vibrations at the proximal end of transducer 100 are opposed by inertial mass 80, longitudinally exerting forces on transducer 100. A resulting electrical signal is provided at any convenient connection points 86 and 91, on respective opposing faces of single element transducer 100, through respective lead wires 92 and 93 to electronics unit 95.

Figure 7:
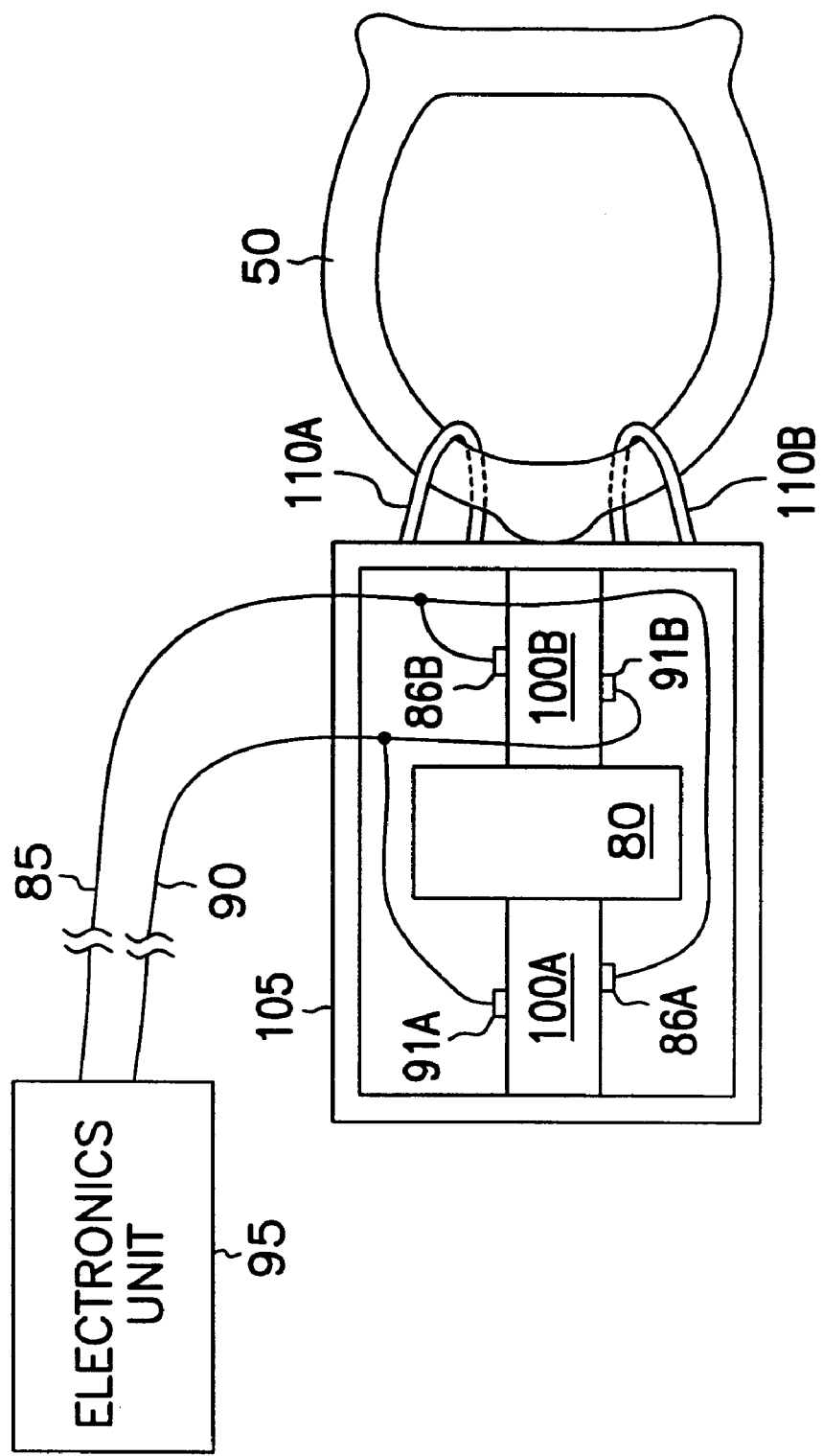
FIG. 7 is a cross-sectional illustration of a fifth embodiment of the invention, including a carrier and also including an inertial mass interposed between two single element transducers.

FIG. 7 illustrates generally a cross-sectional view of a fifth embodiment of the invention, used as an electromechanical output transducer, as described above. A proximal portion of a carrier 105 is secured only to an auditory element, such as stapes 50, by any known attachment technique, as described above. For example, deformable wires 110A–B, secured to carrier 105, may looped through an inner portion of stapes 50 and crimped to secure carrier 105 to stapes 50. The exact technique of attachment is not part of the present invention, except that carrier 105 should be coupled only to the auditory element; it need not be secured elsewhere within the middle ear 35 such as to the temporal bone.

Carrier 105 has opposing interior faces, between which are interposed first and second single element transducers 100A–B, which are respectively mechanically coupled to a distal and a proximal interior face of carrier 105. Inertial mass 80 is interposed between and mechanically coupled to single element transducers 100A–B. This embodiment uses a piezoelectric effect with displacement approximately orthogonal to the direction of an applied electrical input signal, although a piezoelectric effect in another direction may also be used at the designer's discretion by rearranging the connection points accordingly. Electronics unit 95 couples an electrical signal through lead wires 85 and 90 to connection points 86A–B and 91A–B. Connection points 86A–B and 91A–B are pairwise located wherever convenient on opposing faces of first and second single element transducers 100A–B, as illustrated in FIG. 7.

First and second single element transducers 100A–B receive opposite polarity electrical signals from electronics unit 95. For example, lead wire 85 is coupled at connection point 86B to a top face of single element transducer 100B and at connection point 86A to a bottom face of single element transducer 100A. Also, lead wire 90 is coupled at connection point 91B to a bottom face of single element transducer 100B and at connection point 91A to a top face of single element transducer 100A.

In response to a received electrical signal of a first polarity, single element transducer 100A expands longitudinally while single element transducer 100B contracts longitudinally. In response to a received electrical signal of a second polarity, opposite to the first polarity, single element transducer 100A contracts longitudinally while single element transducer 100B expands longitudinally. Thus, single element transducers 100A–B undergo opposite longitudinal deformations in concert to vibrate inertial mass 80. Vibration of inertial mass 80 results in a corresponding opposing vibration of carrier 105 and stapes 50, each of which are mechanically coupled to inertial mass 80.

Carrier 105 is proportioned for disposition within middle ear 35, and is constructed from any known biocompatible material, such as titanium. Carrier 105 is optionally hermetically sealed to protect any enclosed transducer elements and inertial mass from humidity and bodily fluids, providing feedthroughs for lead wires, such as lead wires 85 and 90, for coupling electrical signals through the hermetically sealed enclosure.

Figure 8A:
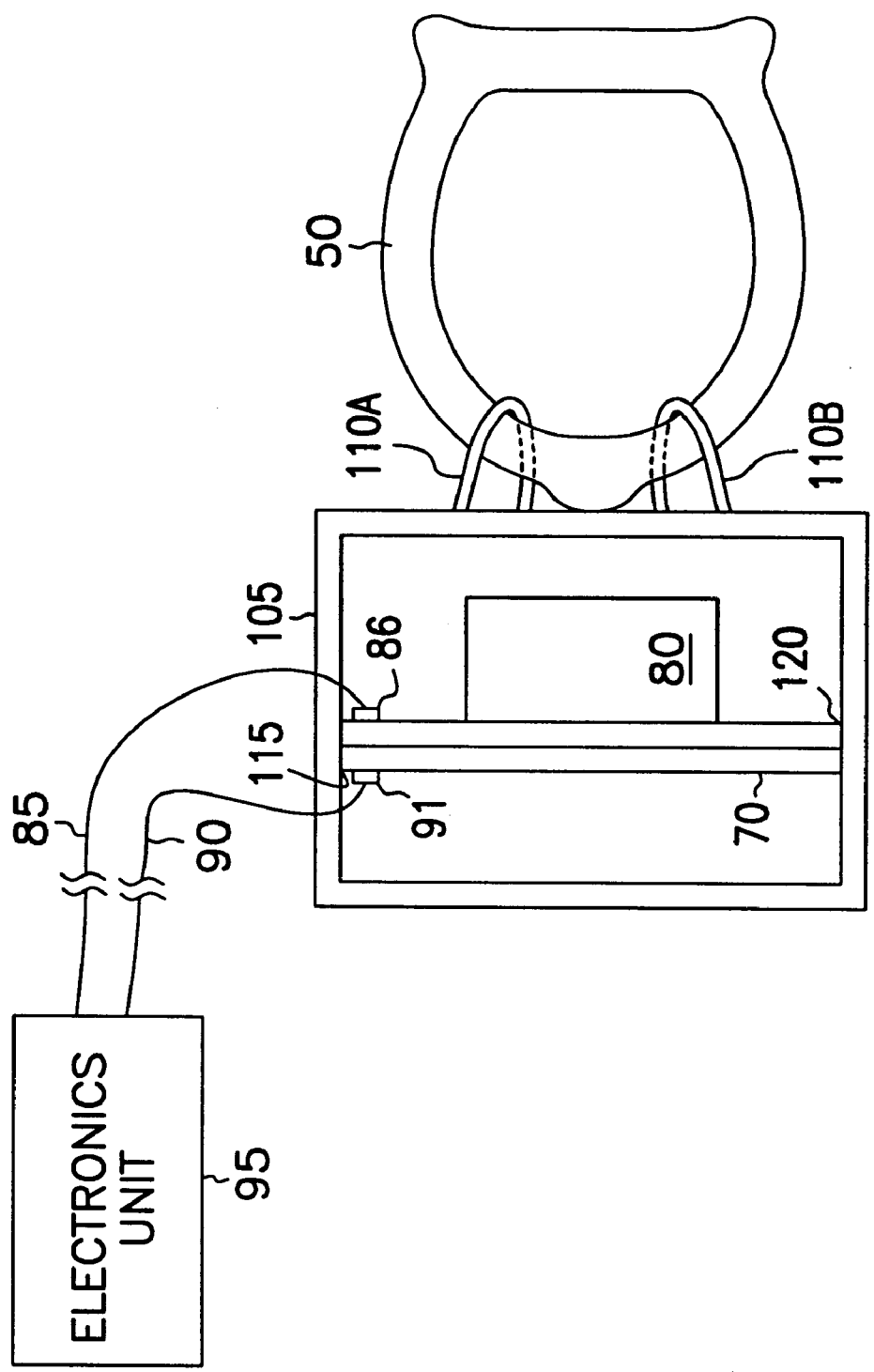
FIG. 8A is a cross-sectional illustration of a sixth embodiment of the invention, including a carrier, a bi-element transducer, and an inertial mass.

FIG. 8A illustrates generally a cross-sectional view of a sixth embodiment of the invention, used as an electromechanical output transducer, as described above. Bi-element transducer 70 is interposed between opposing interior faces of carrier 105. Bi-element transducer 70 is secured to opposing interior faces of carrier 105, such as at points 115 and 120, by any known attachment technique, including adhesives, mechanical fasteners, conforming or interlocking receptacles on carrier 105, or any other such attachment technique. Inertial mass 80 is secured to one of the opposing elements of bi-element transducer 70 by an adhesive, or by any other attachment technique. Electronics unit 95 couples an electrical signal through lead wires 85 and 90 to respective connection points 86 and 91 located wherever convenient on respective opposing elements of bi-element transducer 70.

In response to the received electrical signal, bi-element transducer 70 bends with respect to a longitudinal plane between its opposing elements. The bending is opposed by inertial mass 80, thus mechanically coupling a vibratory force to stapes 50, which is in turn transmitted to cochlea 60 at oval window 55.

Figure 8B:
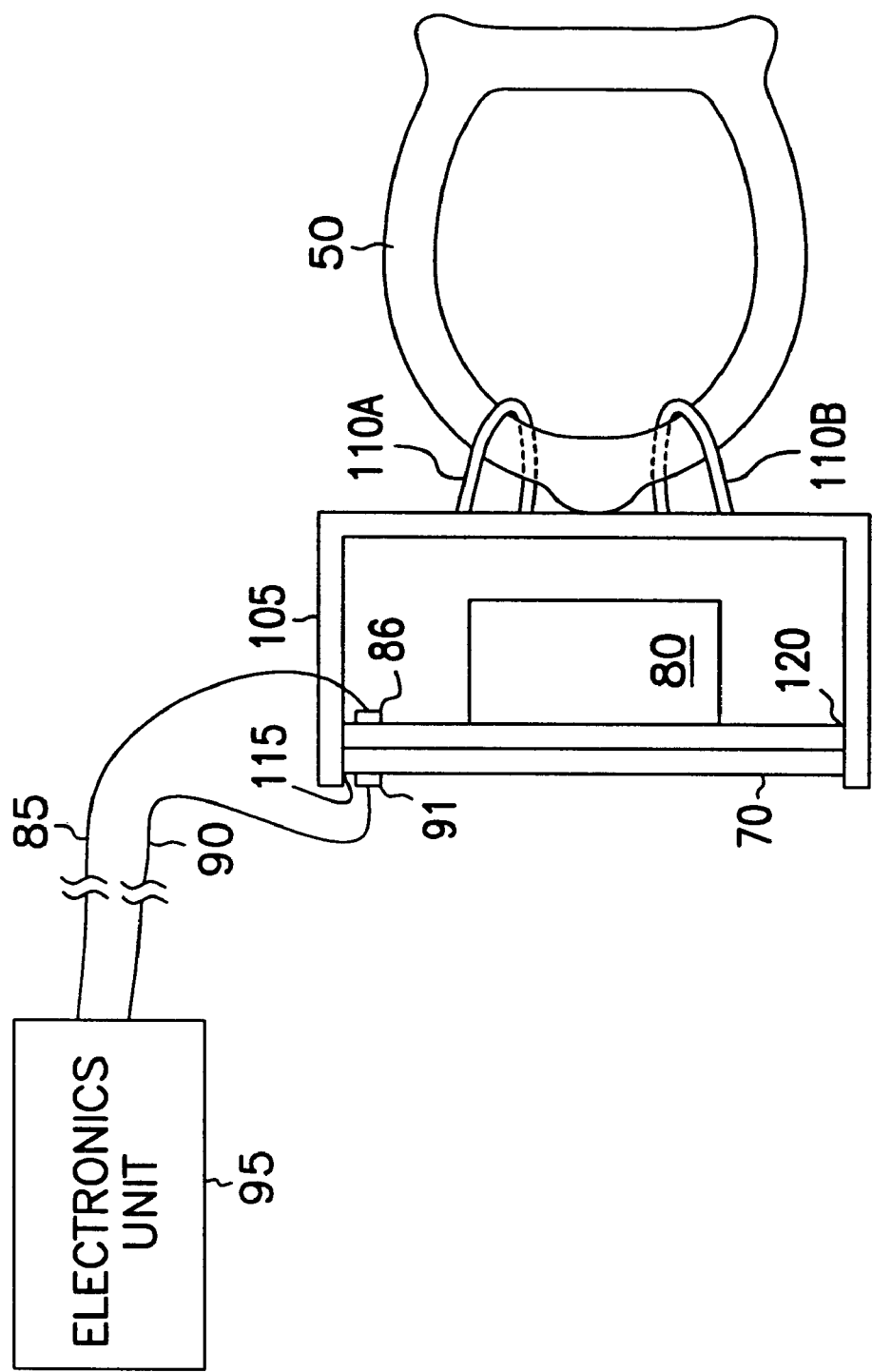
FIG. 8B is a cross-sectional illustration of a further embodiment of the invention, including a carrier that does not enclose the bi-element transducer and inertial mass.

FIG. 8B illustrates generally a cross-sectional view of a further embodiment in which carrier 105 provides support to bi-element transducer 70, but does not hermetically seal or otherwise enclose bi-element transducer 70 or inertial mass 80.

Figure 9:
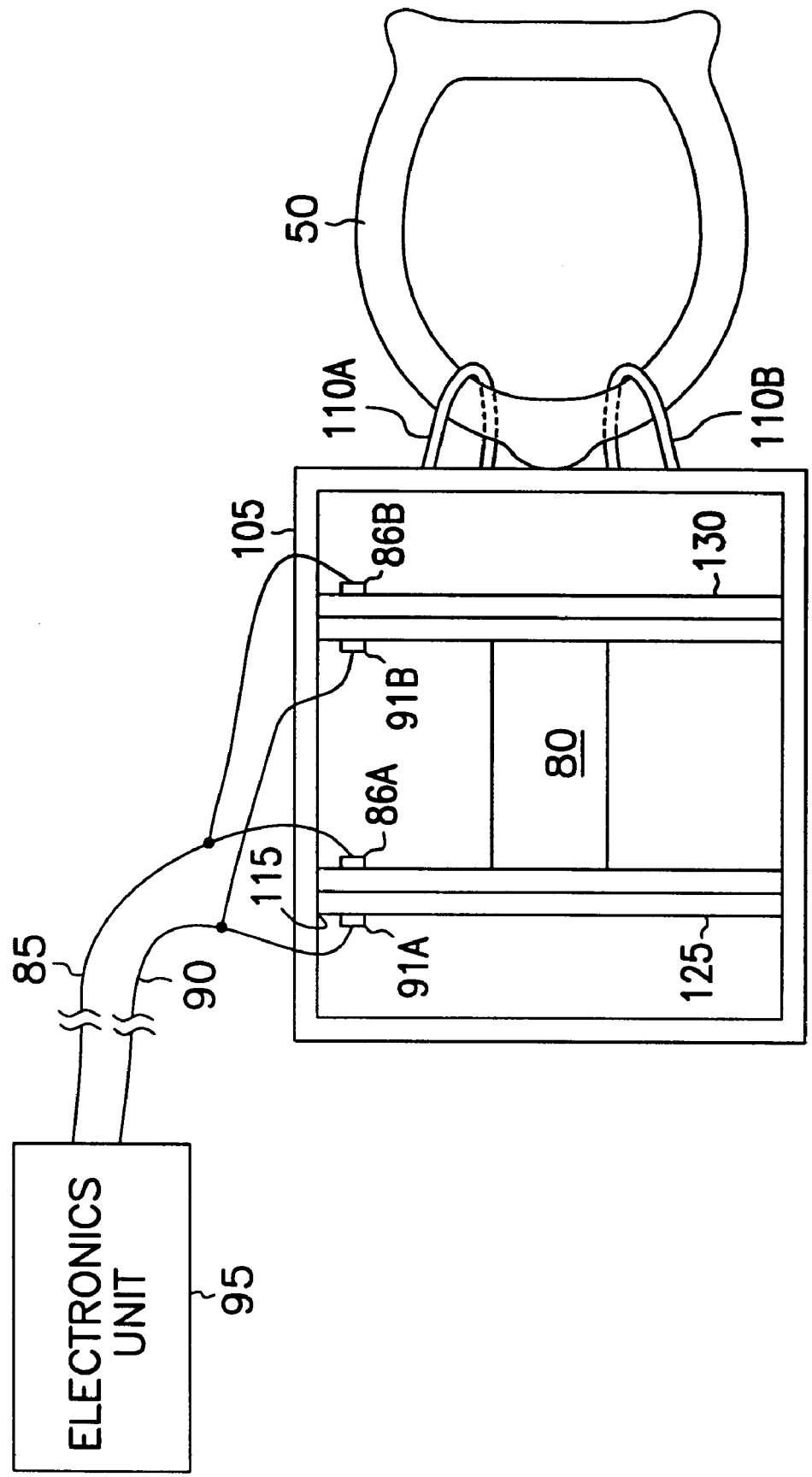
FIG. 9 is a cross-sectional illustration of a seventh embodiment of the invention, including a carrier and also including an inertial mass secured between two bi-element transducers.

FIG. 9 illustrates generally a cross-sectional view of a seventh embodiment of the invention, used as an electromechanical output transducer as described above. First and second bi-element transducers 125 and 130 are each interposed between opposing interior faces of carrier 105. First and second bi-element transducers 125 and 130 are secured to opposing interior faces of carrier 105 by any known attachment technique, as described above. Inertial mass 80 is secured to facing elements of each of first and second bi-element transducers 125 and 130 by an adhesive, or by any other attachment technique. Electronics unit 95 couples an electrical signal through lead wires 85 and 90 to connection points 86A–B and 91A–B, pairwise located wherever convenient on respective opposing elements of respective first and second bi-element transducers 125 and 130.

First and second bi-element transducers 125 and 130 have substantially parallel respective longitudinal planes between their respective opposing elements. In response to the received electrical signal, first and second bi-element transducers 125 and 130 each bend in the same direction with respect to their longitudinal planes. The bending of each of first and second bi-element transducers 125 and 130 vibrates inertial mass 80 and mechanically couples a force to stapes 50, which is in turn transmitted to cochlea 60 at oval window 55.

Figure 10:
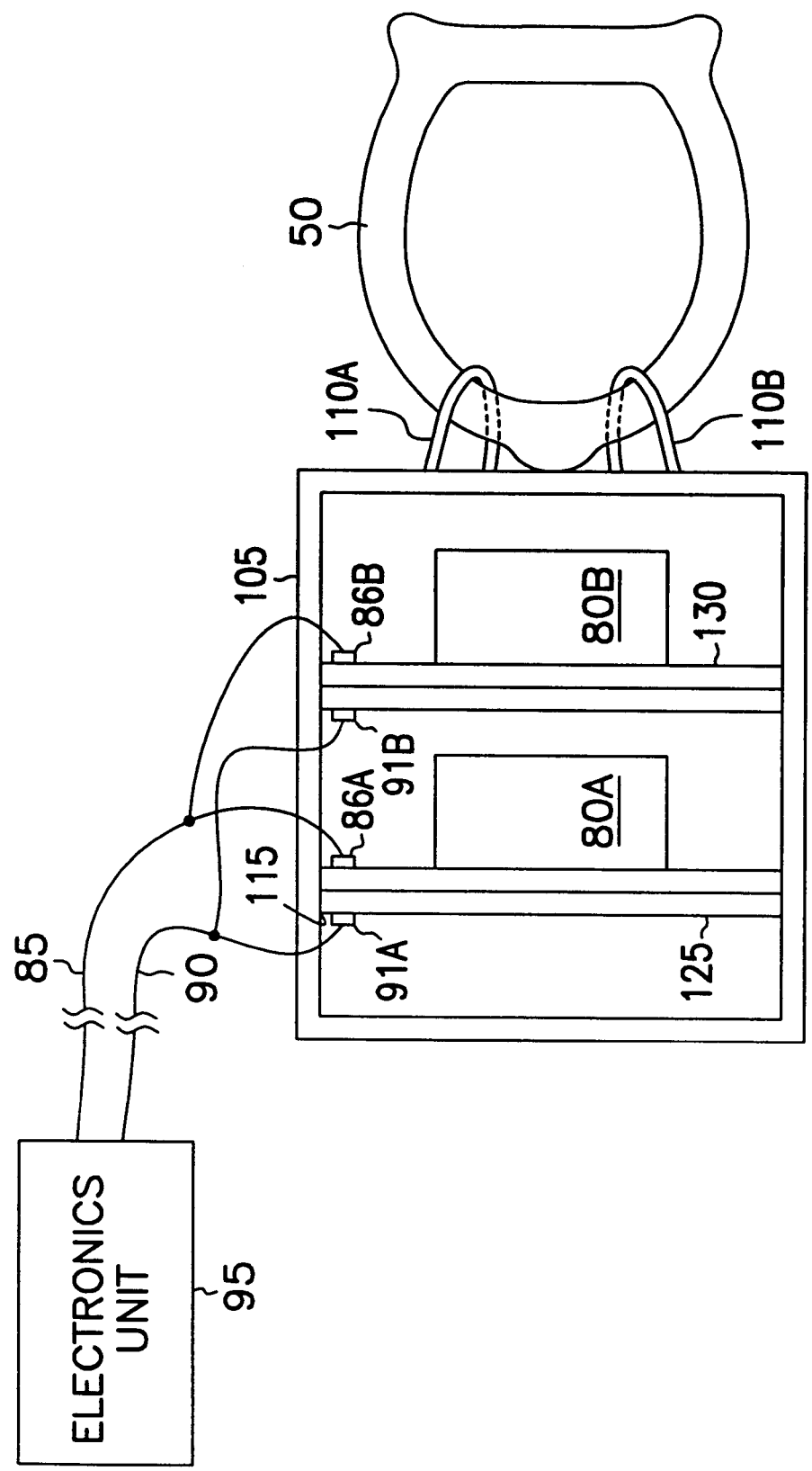
FIG. 10 is a cross-sectional illustration of an eighth embodiment of the invention, including a carrier, two bi-element transducers, and two inertial masses.

FIG. 10 illustrates generally a cross-sectional view of an eighth embodiment of the invention, used as an electromechanical output transducer, as described above. First and second bi-element transducers 125 and 130 are each interposed between opposing interior faces of carrier 105. First and second bi-element transducers 125 and 130 are secured to opposing interior faces of carrier 105 by any known attachment technique, as described above. First inertial mass 80A is secured to one of the opposing individual elements of first bi-element transducer 125. Second inertial mass 80B is secured to one of the opposing individual elements of bi-element transducer 130. Electronics unit 95 couples an electrical signal through lead wires 85 and 90 to connection points 86A–B and 91A–B, pairwise located wherever convenient on respective opposing elements of respective first and second bi-element transducers 125 and 130.

In response to the received electrical signal, first and second bi-element transducers 125 and 130 each bend in the same direction with respect to their substantially parallel respective longitudinal planes, described above. The bending of each of first and second bi-element transducers 125 and 130 is opposed by first and second inertial masses 80A–B, thus mechanically coupling a vibratory force to stapes 50, which is in turn transmitted to cochlea 60 at oval window 55.

In one embodiment, first and second inertial masses 80A–B have substantially nonidentical masses, resulting in different frequency responses of each of first and second inertial masses in combination with respective first and second bi-element transducers 125 and 130. Masses are selected to improve a combined vibration frequency response of carrier 105 resulting from the superposition of the individual frequency responses described above. For example, in the embodiment of FIG. 10, inertial mass 80A is less massive than inertial mass 80B, such that the vibration effected with inertial mass 80A contains more high frequency components than the vibration effected with inertial mass 80B.

Other techniques of implementing different vibration frequency responses could also be used. For example, first and second bi-element transducers 125 and 130 may be selected to vibrate with substantially nonidentical frequency responses. First and second bi-element transducers 125 and 130 could also be supplied with individual input electrical signals having different frequency characteristics. Substantially nonidentical frequency responses could be obtained from first and second bi-element transducers 125 and 130 by using transducers of different physical dimensions, different number of transducer elements, different material properties, different mounting techniques, or any other technique. For example, different mounting techniques can be used to obtain substantially nonidentical frequency responses by cantilevering first bi-element transducer 125 from a single interior face of carrier 105, and securing second bi-element transducer 130, as described above and shown in FIG. 10, to two opposing interior faces of carrier 105.

Figure 11A:
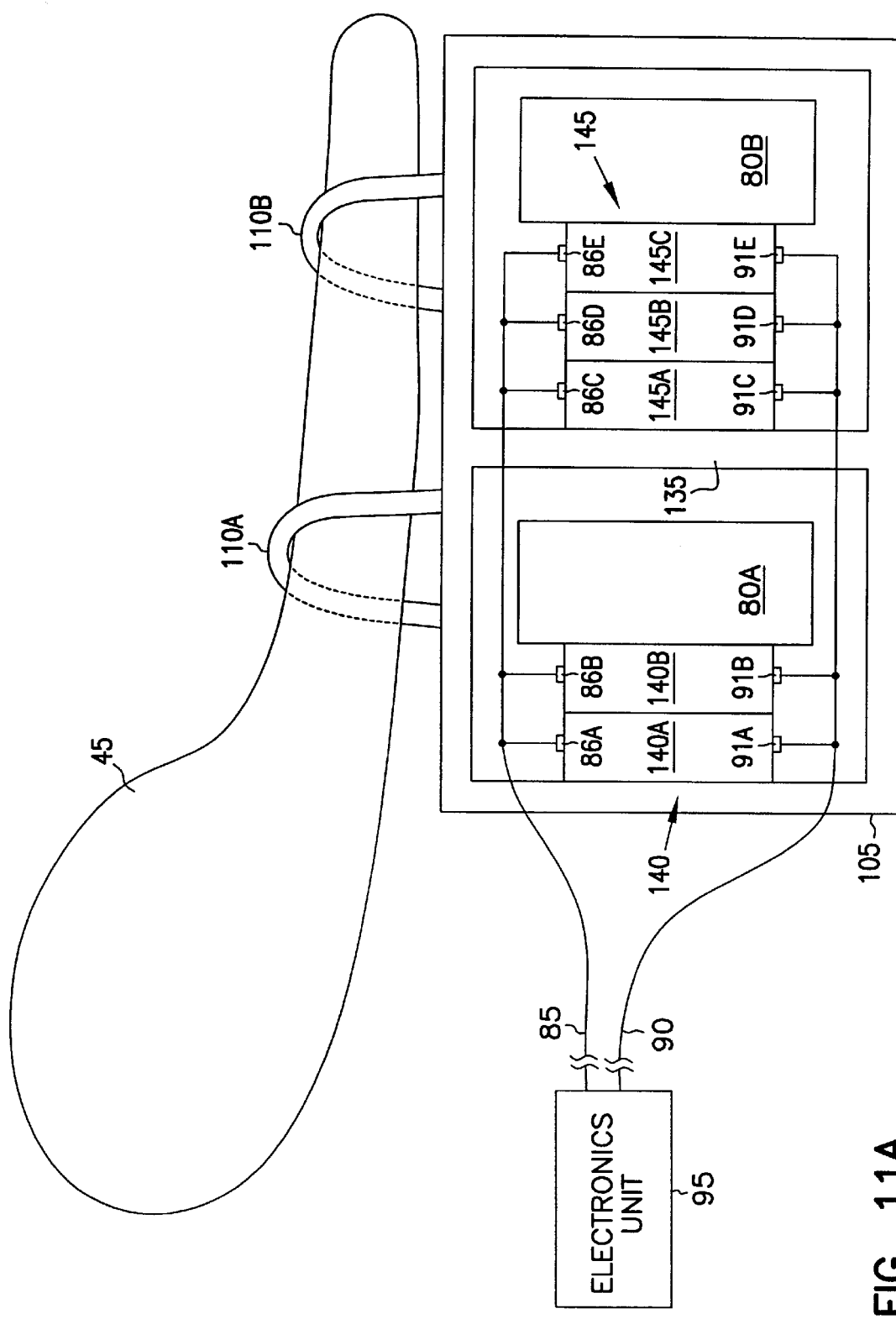
FIG. 11A is a cross-sectional illustration of a ninth embodiment of the invention, including a carrier, two stacked transducers, and two inertial masses.

FIG. 11A illustrates generally a cross-sectional view of a ninth embodiment of the invention used as an electromechanical output transducer, as described above. Carrier 105 is secured only to an auditory element, such as incus 45, by any known attachment technique, as described above. The exact technique of attachment to the auditory element is not part of the invention, except that carrier 105 should be coupled only to the auditory element; it need not be secured elsewhere within the middle ear 35 such as to the temporal bone. In this embodiment, carrier 105 includes support 135. Piezoelectric transducer elements in this embodiment include first stacked transducer 140, secured to an interior face of carrier 105, and second stacked transducer 145, secured to support 135. First inertial mass 80A is secured only to first stacked transducer 140. Second inertial mass 80B is secured only to second stacked transducer 145.

First and second stacked transducers 140 and 145 comprise a selectable number of transducer subelements, such as 140A–B and 145A–C respectively, stacked mechanically in series. In one embodiment, first and second stacked transducers 140 and 145 have different numbers of transducer subelements, resulting in different vibration frequency responses such that an overall frequency response bandwidth of carrier 105 is increased. Other techniques may also be used to obtain different frequency responses, as described above.

Electronics unit 95 couples an electrical signal through lead wires 85 and 90 to connection points 86A–E and 91A–E located wherever convenient on respective opposing faces of each of first and second transducer subelements 140A–B and 145A–C. This embodiment uses a piezoelectric effect with displacement approximately orthogonal to the direction of an applied electrical input signal, although a piezoelectric effect in another direction may also be used at the designer's discretion by rearranging the connection points accordingly.

In response to the received electrical signal, first and second stacked transducers 140 and 145 each expand and contract in concert in a longitudinal direction approximately normal to their respective approximately planar interfaces with first and second inertial masses 80A–B. As a result, first and second inertial masses 80A–B vibrate. This mechanically couples an opposing force through carrier 105 to stapes 50, which is in turn transmitted to cochlea 60 at oval window 55.

FIG. 11B illustrates generally an alternative embodiment to that illustrated in FIG. 11A. This embodiment uses a piezoelectric effect with displacement approximately the same direction of an applied electrical input signal, although a piezoelectric effect in another direction may also be used at the designer's discretion by rearranging the connection points accordingly. Electronics unit 95 couples an electrical signal through lead wires 85 and 90 to connection points 87A–D and 92A–C located across a length of each of transducer subelements 140A–B and 145A–C in the longitudinal direction between proximal and distal portions of carrier 105.

In response to the received electrical signal, first and second stacked transducers 140 and 145 each expand and contract in concert in a longitudinal direction approximately normal to their respective approximately planar interfaces with first and second inertial masses 80A–B. As a result, first and second inertial masses 80A–B vibrate. This mechanically couples an opposing force through carrier 105 to stapes 50, which is in turn transmitted to cochlea 60 at oval window 55.

Figure 12A:
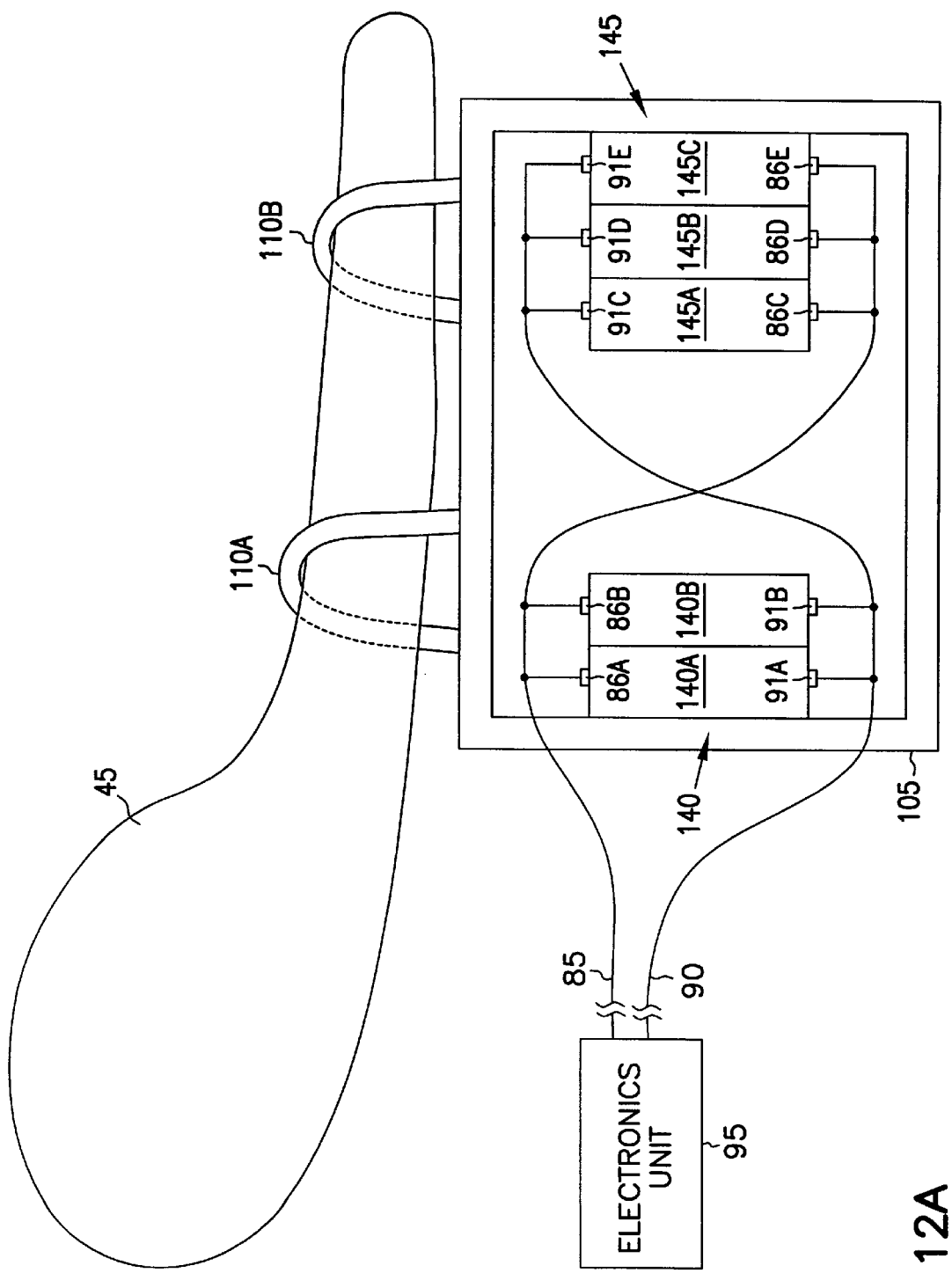
FIG. 12A is a cross-sectional illustration of a tenth embodiment of the invention, including a carrier and also including two stacked transducers secured within its opposing faces.

FIG. 12A illustrates generally a cross-sectional view of a tenth embodiment of the invention used as an electromechanical output transducer, as described above. In this embodiment, first and second stacked transducers 140 and 145 are secured to carrier 105 at its opposing interior faces, such that a direction approximately orthogonal to the plane of each of the opposing interior faces is in the direction of vibratory motion of the auditory element to which carrier 105 is secured. In this embodiment, inertial masses 80A–B are omitted; vibrations of the distributed masses of first and second stacked transducers 140 and 145 mechanically couple a force through carrier 105 to stapes 50.

This embodiment uses a piezoelectric effect with displacement approximately orthogonal to the direction of an applied electrical input signal, although a piezoelectric effect in another direction may also be used at the designer's discretion by rearranging the connection points accordingly. Electronics unit 95 couples an electrical signal through lead wires 85 and 90 to connection points 86A–E and 91A–E, pairwise located on respective opposing faces of each of first and second transducer subelements 140A–B and 145A–C. Since first and second stacked transducers 140 and 145 are secured to opposing interior faces of carrier 105, first and second stacked transducers 140 and 145 receive opposite polarity electrical signals from electronics unit 95. For example, lead wire 85 is coupled at connection points 86A–B to a top face of stacked transducer 140 and at connection points 86C–E to a bottom face of stacked transducer 145. Also, lead wire 90 is coupled at connection points 91A–B to a bottom face of stacked transducer 140 and at connection points 91 C–E to a top face of stacked transducer 145.

In response to a received electrical signal of a first polarity, stacked transducer 140 expands longitudinally while stacked transducer 145 contracts longitudinally. In response to a received electrical signal of a second polarity, opposite to the first polarity, stacked transducer 140 contracts longitudinally while stacked transducer 145 expands longitudinally. Thus, stacked transducers 140 and 145 undergo opposite longitudinal deformations in concert to vibrate carrier 105 and incus 45.

Figure 12B:
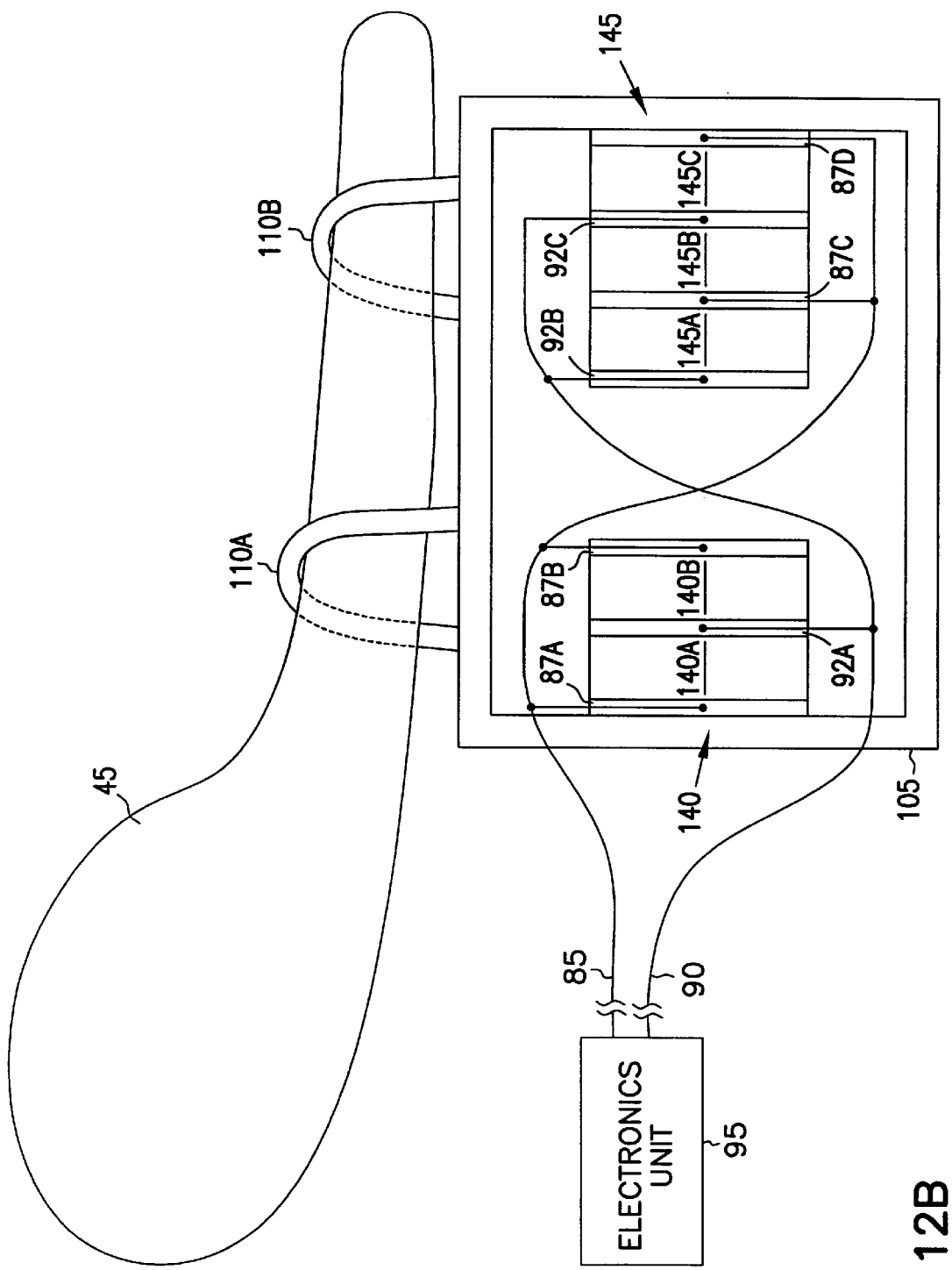
FIG. 12B is a cross-sectional illustration of an alternative embodiment, to FIG. 12A, having electrical connections across a length of each transducer subelement.

FIG. 12B illustrates generally an alternative embodiment to that illustrated in FIG. 12A. This embodiment uses a piezoelectric effect with displacement approximately the same direction of an applied electrical input signal, although a piezoelectric effect in another direction may also be used at the designer's discretion by rearranging the connection points accordingly. Electronics unit 95 couples an electrical signal through lead wires 85 and 90 to connection points 87A–D and 92A–C located across a length of each of transducer subelements 140A–B and 145A–C in the longitudinal direction between proximal and distal portions of carrier 105.

As described above, first and second stacked transducers 140 and 145 receive opposite polarity electrical signals from electronics unit 95. In response to a received electrical signal of a first polarity, stacked transducer 140 expands longitudinally while stacked transducer 145 contracts longitudinally. In response to a received electrical signal of a second polarity, opposite to the first polarity, stacked transducer 140 contracts longitudinally while stacked transducer 145 expands longitudinally. Thus, stacked transducers 140 and 145 undergo opposite longitudinal deformations in concert to vibrate carrier 105 and incus 45.

FIG. 13A illustrates generally a cross-sectional view of an eleventh embodiment of the invention used as an electromechanical output transducer, as described above. In this embodiment, first and second stacked transducers 150 and 155 are cylindrical shaped having cylindrically hollowed cores. Since first and second stacked transducers 150 and 155 are on opposing interior faces of carrier 105, electronics unit 95 provides through lead wires 85 and 90 opposite polarity electrical input signals to first and second stacked transducers 150 and 155 at connection points 86A–E and 91A–E. For example, lead wire 85 is coupled at connection points 86A–B to an outer face of stacked transducer 150 and at connection points 86C–E to an interior face within the hollow core of stacked transducer 155. Also, lead wire 90 is coupled at connection points 91A–B to an interior face within the hollow core of stacked transducer 150 and at connection points 91C–E to an outer face of stacked transducer 145.

Thus, stacked transducers 150 and 155 undergo opposite longitudinal deformations in concert to vibrate carrier 105 and incus 45. FIG. 13B illustrates generally a cross-sectional view the invention of FIG. 13A, along the cut line illustrated in FIG. 13A. FIG. 13B further illustrates a hollow cylindrical core region 160 within second stacked transducer 155.

The embodiment of FIGS. 13A–B could also be used as an electromechanical input transducer, as described above, by securing carrier 105 only to a vibrating auditory element, such as incus 45, and preferably isolating the vibrating auditory element from any auditory element vibrated by an electromechanical output transducer.

Figure 14:
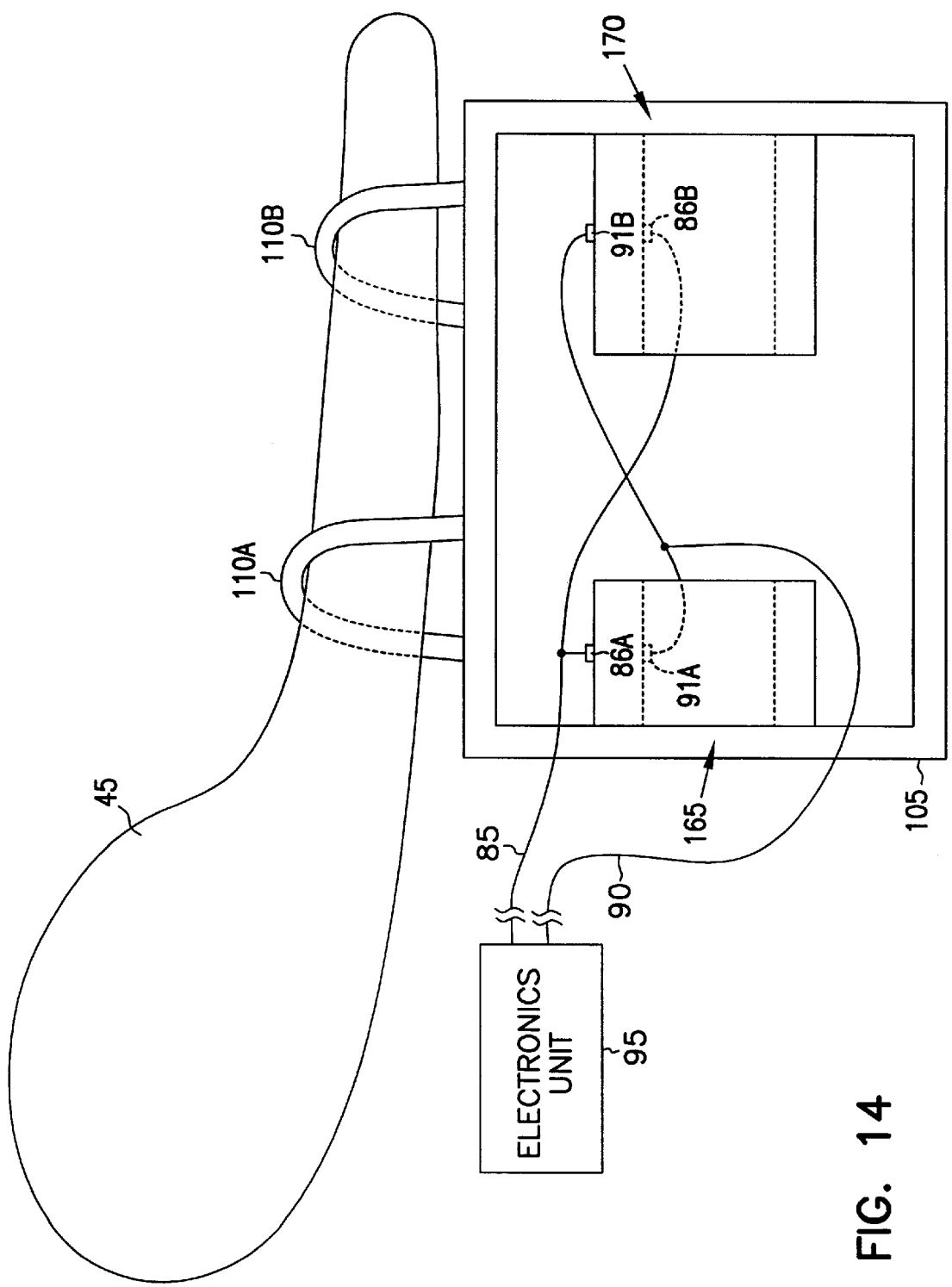
FIG. 14 is a cross-sectional view of a twelfth embodiment of the invention, including a carrier and also including two single element transducers having cylindrically hollowed cores.

FIG. 14 illustrates generally a cross-sectional view of an twelvth embodiment of the invention used as an electromechanical output transducer, as described above. In this embodiment, first and second single element transducers 165 and 170 are cylindrical shaped having cylindrical hollow cores. First and second single element transducers receive opposite polarity electrical input signals at connection points 86A–B and 91A–B at outer faces and at inner faces within their hollow cylindrical cores, as illustrated. Thus, stacked transducers 165 and 170 undergo opposite longitudinal deformations in concert to vibrate carrier 105 and incus 45.

Figure 15:
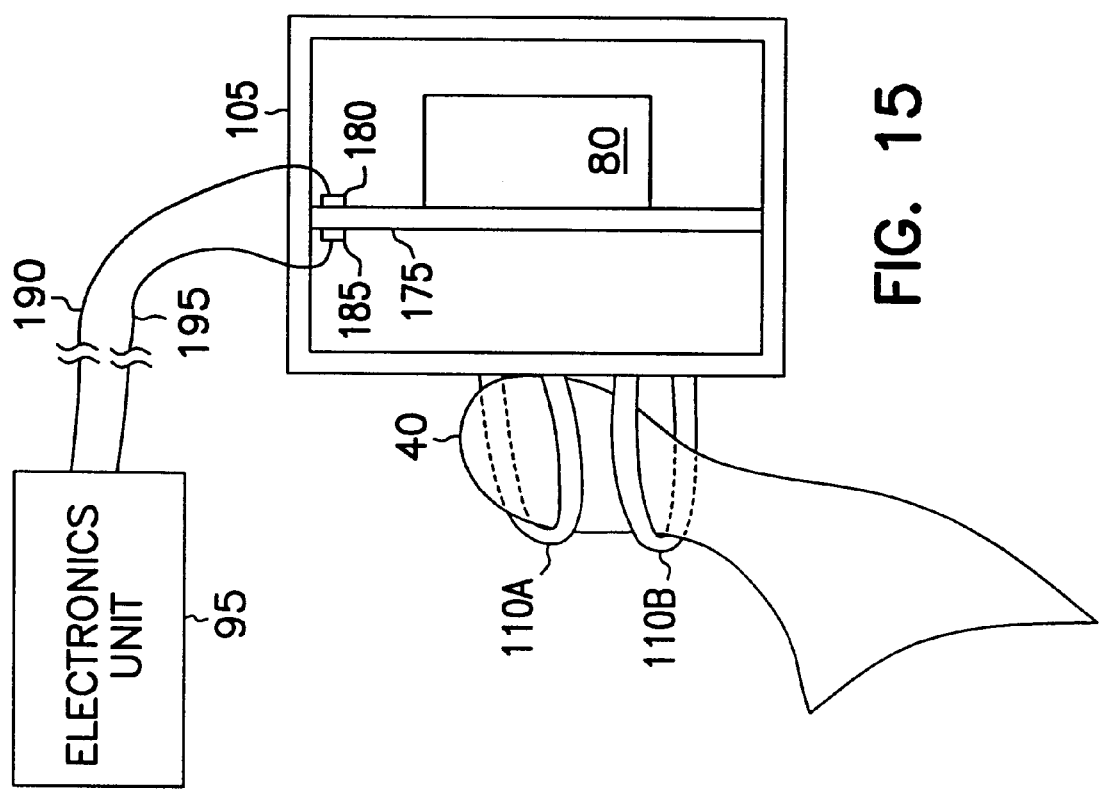
FIG. 15 is a cross-sectional view of a thirteenth embodiment of the invention, secured to a vibrating malleus, including a carrier, a film transducer, and an inertial mass.

FIG. 15 illustrates generally a cross-sectional view of an thirteenth embodiment of the invention, used as an electromechanical input transducer. Carrier 105 is secured only to an auditory element, such as malleus 40, by any known attachment technique, as described above. The exact technique of attachment to the auditory element is not part of the present invention, except that carrier 105 should be coupled only to the auditory element from which vibrations are sensed; it need not be secured elsewhere within the middle ear 35 such as to the temporal bone.

Piezoelectric film transducer 175 is interposed between opposing interior faces of carrier 105. Film transducer 175 comprises a highly piezoelectric film such as a polarized fluoropolymer, e.g. polyvinylidene fluoride (PVDF). For this application, a PVDF film such as that sold under the trademark "Kynar" by AMP, Inc., of Harrisburg, Pa., is the preferred material for film transducer 175.

Film transducer 175 is secured to opposing interior faces of carrier 105 by any known attachment technique, such as described above. Inertial mass 80 is secured to film transducer 175 by an adhesive, or by any other known attachment technique. Mechanical vibrations of malleus 40 are coupled to inertial mass 80 through carrier 105 and film transducer 175. Inertial mass 80 opposes the mechanical vibrations, thus bendingly deforming film transducer 175. A resulting output electrical signal is received across a film thickness at connection points 180 and 185, and coupled to input terminals of electronics unit 95 through respective leads 190 and 195.

Figure 16:
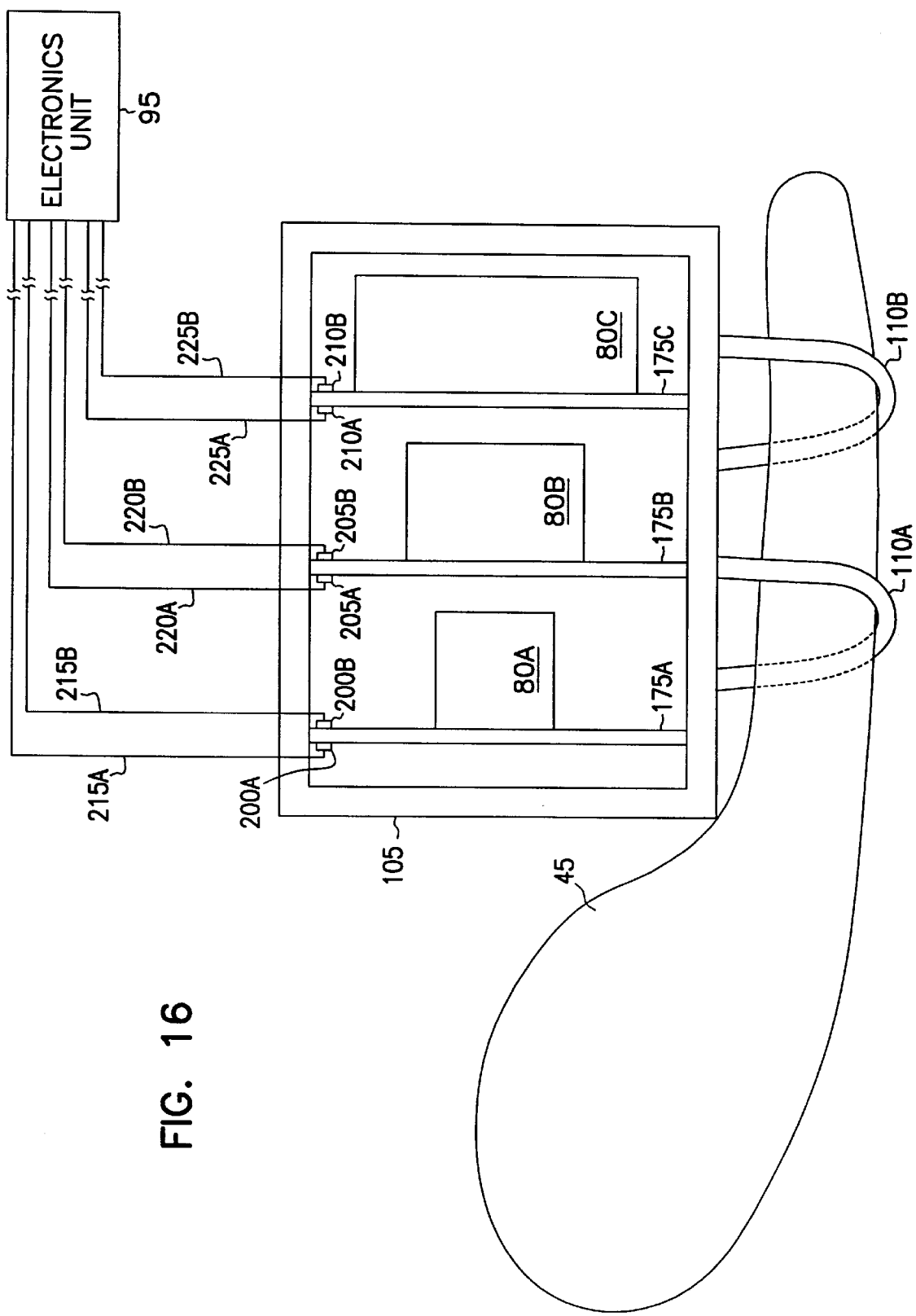
FIG. 16 is a cross-sectional view of a fourteenth embodiment of the invention, secured to a vibrating incus, including a carrier and a plurality of film transducers and respective inertial masses.

FIG. 16 illustrates generally a cross-sectional view of an fourteenth embodiment of the invention, used as an electromechanical input transducer, as described above. Carrier 105 is secured only to a vibrating auditory element, such as incus 45. The vibrating auditory element is preferably mechanically isolated from any auditory element vibrated by an electromechanical output transducer.

In this embodiment, the piezoelectric elements comprise a plurality of piezoelectric film transducers 175A–C, selectable in number, each interposed between and secured to opposing interior faces of carrier 105. Film transducers 175A–C comprise a highly piezoelectric film such as PVDF. Inertial masses 80A–C are each secured to respective film transducers 175A–C by an adhesive, or by any other known attachment technique.

Mechanical vibrations of incus 45 are coupled to inertial masses 80A–C through carrier 105 and film transducers 175A–C. The vibrations are opposed by inertial masses 80A–C, each having different masses, thus bendingly deforming film transducers 175A–C. Resulting output electrical signals, which have different frequency characteristics, are produced across each film's thickness at respective connection points 200A–B, 205A–B, 210A–B. The electrical signals at respective connection points 200A–B, 205A–B, 210A–B are coupled through respective leads 215A–B, 220A–B, and 225A–B to input terminals of electronics unit 95 for summing and further processing.

Figure 17:
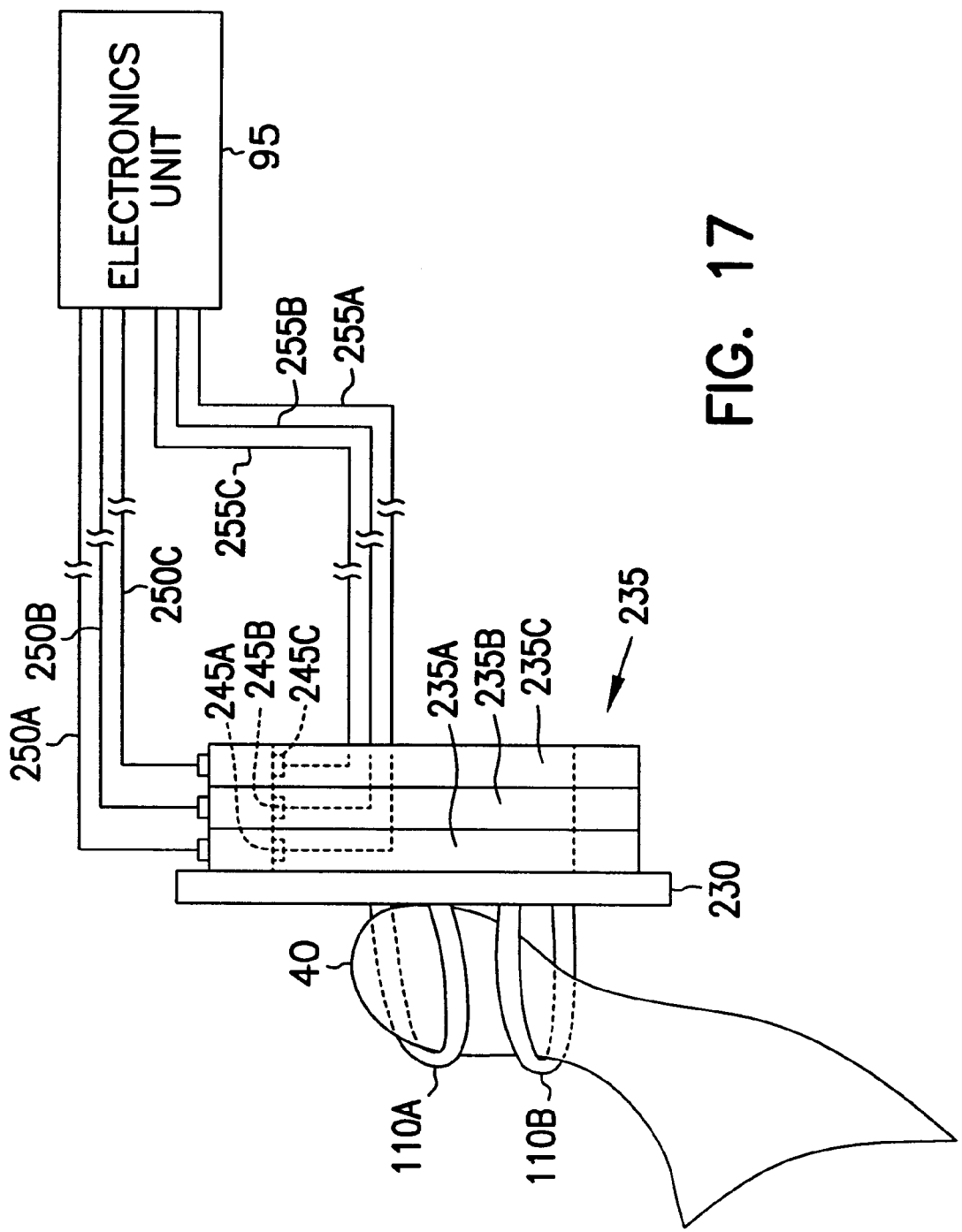
FIG. 17 is a cross-sectional view of a fifteenth embodiment of the invention, secured to a vibrating malleus, including a carrier and also including a stacked transducer having a cylindrically hollowed core.

FIG. 17 illustrates generally a cross-sectional view of an fifteenth embodiment of the invention, used as an electromechanical input transducer, as described above. Carrier 230, comprising an approximately planar mechanical frame, is secured only to a vibrating auditory element, such as malleus 40. In this embodiment, a piezoelectric element comprises stacked transducer 235, which is secured to carrier 230, as described above. Stacked transducer 235 comprises a selectable number of subelements, such as 235A–C, each of which are cylindrical shaped having coincidental cylindrical hollow cores, as described above.

Mechanical vibrations of malleus 40 are mechanically coupled to stacked transducer 235 through carrier 230. A resulting individual electrical signal is provided by each subelement 235A–C between a first connection point 240A–C on its outer face, and a second connection point 245A–C on its interior face within the hollow core of stacked transducer 235. First and second connection points 240A–C and 245A–C are coupled through lead wires 250A–C and 255A–C to electronics unit 95 for summing and further processing.

Figure 18:
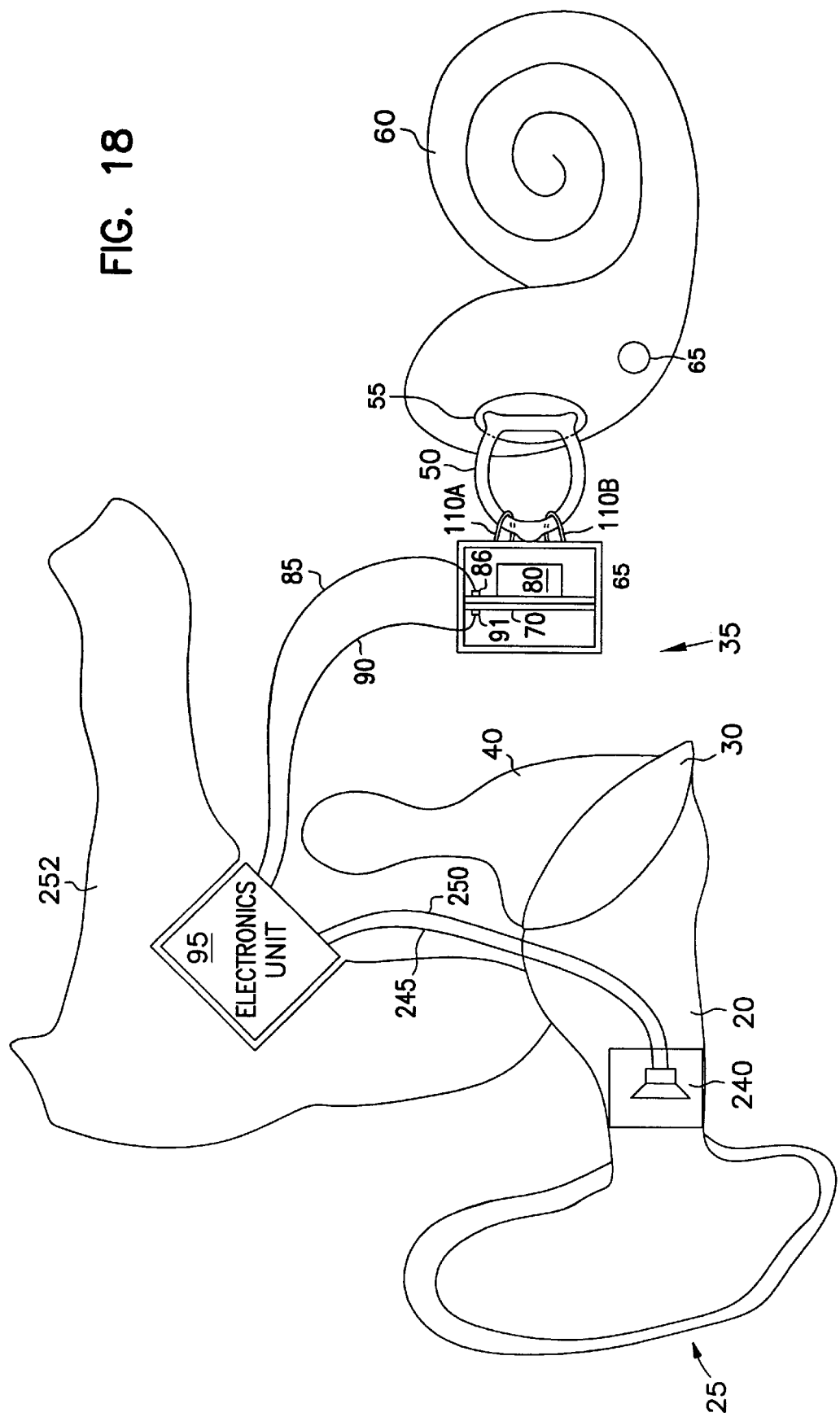
FIG. 18 is a cross-sectional view of the sixteenth embodiment of the invention, in use with a P-MEI hearing aid having a microphone in the external auditory canal.

FIG. 18 illustrates generally a cross-sectional view of the sixteenth embodiment of the invention, described above, in use with a particular type of P-MEI hearing aid. In FIG. 18, a microphone 240 in external auditory canal 20 transduces acoustic energy into an electrical signal provided through input leads 245 and 250 to electronics unit 95 implanted in a mastoid portion of the temporal bone 252. Alternatively, electronics unit 95 may be located outside the skull such as behind outer ear 25. Electronics unit 95 further processes the received electrical signal, and provides an amplified electrical signal through lead wires 85 and 90 at respective connection points 86 and 91 to bi-element transducer 70. Bi-element transducer 70 is secured to carrier 105, which is in turn secured only to a vibrated auditory element such as stapes 50.

Figure 19:
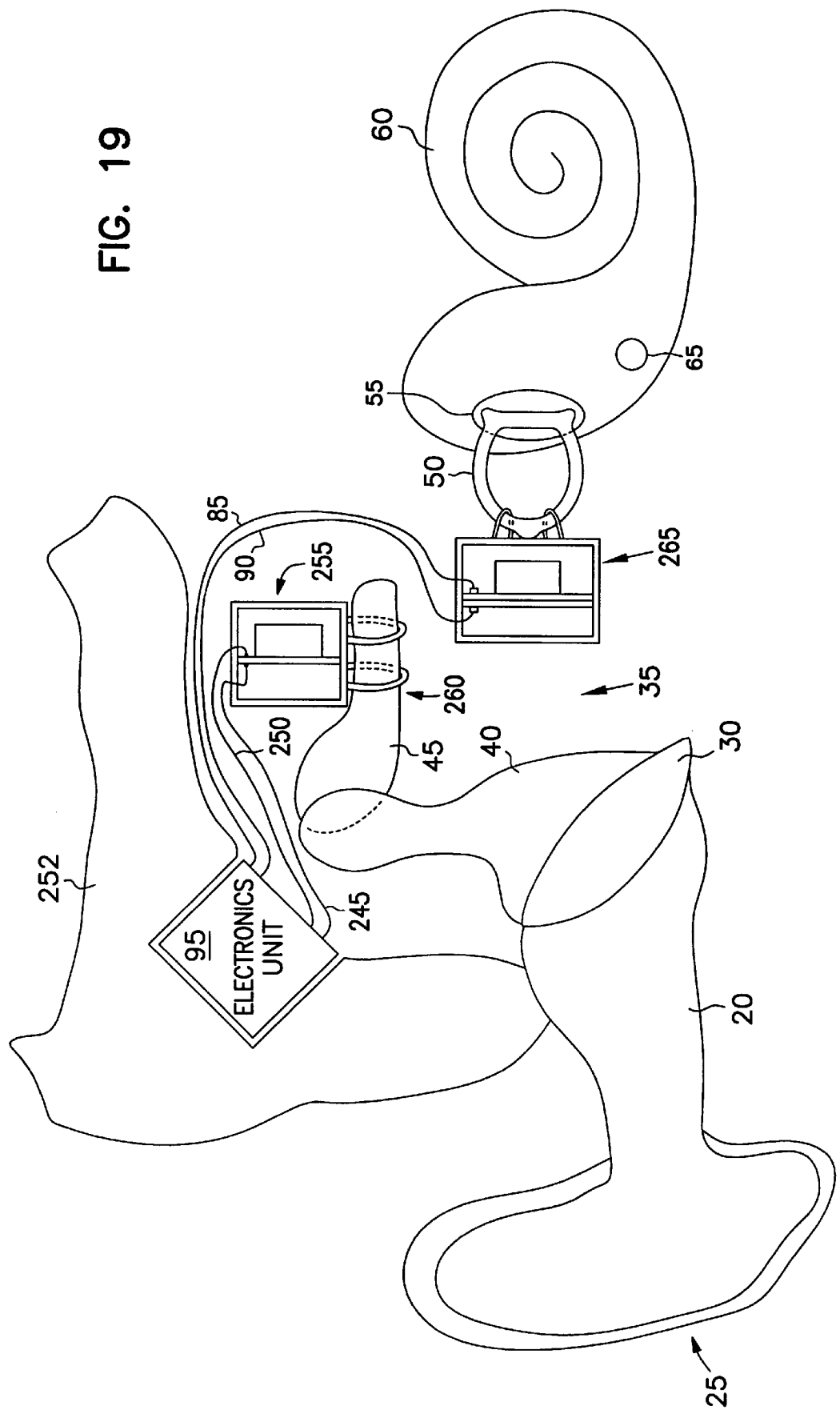
FIG. 19 is a cross-sectional view of a preferred embodiment of the invention, in use with a T-MEI hearing aid, including both electromechanical input and output transducers.

FIG. 19 illustrates generally a cross-sectional view of a highly preferred embodiment of the invention, in use with a particular type of T-MEI hearing aid. In FIG. 19, electromechanical input transducer 255 is secured only to a vibrating auditory element, such as incus 45, which is mechanically isolated, as described above, from stapes 50 by a surgically shortened long arm portion 260. Sensing mechanical vibrations at incus 45 may offer more natural hearing due to the complex nature of the incudomalleolar joint coupling malleus 40 to incus 45. An electromechanical output transducer 265 is secured only to a vibrated auditory element, such as stapes 50. Electromechanical input transducer 255 comprises a piezoelectric film and inertial mass as described above with respect to the thirteenth embodiment of the invention. Electromechanical output transducer 265 comprises a bi-element transducer and inertial mass as described above with respect to the sixth embodiment of the invention.

Mechanical vibrations of the incus 45 are sensed by the electromechanical input transducer 255 and transduced into an electrical signal provided through lead wires 245 and 250 to electronics unit 95 implanted in the mastoid portion of temporal bone 80. Electronics unit 95 further processes the electrical signal and provides an amplified electrical signal through lead wires 85 and 90 to electromechanical output transducer 265. Electromechanical output transducer 265 transduces the amplified electrical signal into a mechanical vibration which is mechanically coupled to the stapes 50, and in turn coupled to the oval window 55 portion of cochlea 60.

For clarity, the above described embodiments have been described with respect to function as either electromechanical input or output transducers. The piezoelectric effect allows both mechanical-to-electrical and electrical-to-mechanical transducing. Accordingly, each of the above described embodiments are intended to function as either electromechanical input transducers for sensing mechanical vibrations, or as electromechanical output transducers for producing mechanical vibrations. In particular, the above described embodiments may be switched between vibrating and vibrated auditory elements to obtain the desired functionality, and electrical signals can be accordingly coupled to an electronics unit of a P-MEI, T-MEI, or other hearing system. For example, the invention could provide middle ear vibration sensing in conjunction with a cochlear implant, or other hearing system having output electrical stimuli. Also, inventive concepts illustrated in particular embodiments are intended to also apply to the other embodiments disclosed herein.

Thus, the invention provides convenient piezoelectric input and output electromechanical transducers, each mounted only to the auditory element for which vibrations are transduced. In particular, the invention does not require mounting a transducer to the temporal bone. This minimizes the invasive complexity of the surgical implantation procedure, and also minimizes steady state forces applied to the auditory element.

What is claimed is:

1. An electromechanical transducer for an implantable hearing aid, the transducer comprising:
   a carrier proportioned for mechanically coupling to a middle ear only through an auditory element in the middle ear;
   a first piezoelectric element mechanically coupled to the carrier for transducing between a mechanical vibration of the carrier and a first electrical signal;
   a second piezoelectric element mechanically coupled to the carrier for transducing between the mechanical vibration of the carrier and a second electrical signal;
   a first inertial mass mechanically coupled to the first piezoelectric element; and
   a second inertial mass mechanically coupled to the second piezoelectric element.

2. The transducer of claim 1, in which the first and second inertial masses have substantially nonidentical masses.

3. The transducer of claim 2, in which the mechanical vibration of the carrier is at least partially produced by a superposition of vibrations from each of a first and second combination, the first combination including the first inertial mass and the first piezoelectric element and having a substantially nonidentical electromechanical frequency response from the second combination, the second combination including the second inertial mass and the second piezoelectric element.

4. The transducer of claim 2, in which the respective first and second electrical signals are transduced from the mechanical vibration of the carrier.

5. An implantable electromechanical device adapted for coupling exclusively only to an auditory element in a human ear for which auditory sound vibrations are transduced, the device comprising:
   first and second bi-element transducers with a first inertial mass attached to said first transducer and a second inertial mass attached to said second transducer;
   means for securely attaching said first and second transducers to the auditory element; and
   an electronics unit to transmit electrical signals to said first and second transducers,
   said electrical signals being sufficient to induce deflections forming vibratory displacements in an orientation relative to a desired directional plane within said first and second piezoelectric elements and said deflections being opposed by a resistance from each of said first and second inertial masses to thereby provide a vibratory frequency response preconditioned to exert a specific resultant vibratory force on the auditory element.

6. The device of claim 5, wherein said first and second inertial masses are substantially different masses to enable different frequency responses in combination with vibratory displacements of said first and second transducers.

7. The device of claim 6, wherein said first and second bi-element transducers are structured to vibrate with substantially nonidentical frequency responses.

* * * * *